United States Patent
Bettens

(10) Patent No.: US 10,390,905 B2
(45) Date of Patent: Aug. 27, 2019

(54) SURGICAL GUIDING TOOL, METHOD AND KIT FOR PLACING DENTAL IMPLANTS

(71) Applicant: Drs. Bettens-De Pooter BVBA, Deurle (BE)

(72) Inventor: Rolf Bettens, Deurle (BE)

(73) Assignee: Drs. Bettens-De Pooter BVBA, Deurle (BE)

( * ) Notice: Subject to any disclaimer, the term of this patent is extended or adjusted under 35 U.S.C. 154(b) by 0 days.

(21) Appl. No.: 15/559,459

(22) PCT Filed: Mar. 21, 2016

(86) PCT No.: PCT/EP2016/056156
§ 371 (c)(1),
(2) Date: Sep. 19, 2017

(87) PCT Pub. No.: WO2016/146852
PCT Pub. Date: Sep. 22, 2016

(65) Prior Publication Data
US 2018/0110584 A1    Apr. 26, 2018

(30) Foreign Application Priority Data
Mar. 19, 2015 (EP) .................................... 15159922

(51) Int. Cl.
*A61C 8/00* (2006.01)
*A61C 1/08* (2006.01)
*A61B 17/17* (2006.01)

(52) U.S. Cl.
CPC ............ *A61C 1/084* (2013.01); *A61C 8/0089* (2013.01); *A61B 17/176* (2013.01)

(58) Field of Classification Search
CPC ....... A61C 1/082; A61C 1/084; A61C 8/0034; A61C 8/0089; A61C 19/04; A61C 3/00
USPC ............................................................ 433/75
See application file for complete search history.

(56) References Cited

U.S. PATENT DOCUMENTS

| | | | |
|---|---|---|---|
| 4,836,781 A * | 6/1989 | Meinershagen | A61C 5/85 433/141 |
| 4,904,183 A * | 2/1990 | Hannan | A61C 7/02 433/3 |
| 5,015,183 A | 5/1991 | Fenick | |
| 5,556,278 A | 9/1996 | Meitner | |

(Continued)

FOREIGN PATENT DOCUMENTS

| | | | |
|---|---|---|---|
| KR | 100726481 B1 * | 6/2007 | |
| KR | 100860762 B1 * | 9/2008 | |

(Continued)

*Primary Examiner* — Wade Miles
*Assistant Examiner* — Matthew P Saunders
(74) *Attorney, Agent, or Firm* — James Creighton Wray

(57) ABSTRACT

A device suitable for the subsequent positioning of a dental implant, having a handle extending along a longitudinal axis and having a proximal and a distal end, and a bifurcated abutment at the distal end and at the proximal end of the handle, each abutment having two legs, whereby the configuration of the two legs on the proximal abutment is mirrored with respect to the configuration on the distal end. At least one bifurcated abutment is adapted to embrace the processus pyramidalis ossis palatini and/or the processus pterygoideus ossis sphenoidalis and/or the tuberosity of the maxilla.

15 Claims, 12 Drawing Sheets

(56) References Cited

U.S. PATENT DOCUMENTS

| | | | | |
|---|---|---|---|---|
| 6,575,749 B1 * | 6/2003 | Greenwald | ............... | A61C 3/00 |
| | | | | 433/141 |
| 7,086,860 B2 | 8/2006 | Schuman | | |
| 7,097,451 B2 | 8/2006 | Tang | | |
| 2002/0151769 A1 * | 10/2002 | Kim | ................ | A61B 17/02 |
| | | | | 600/210 |
| 2010/0151411 A1 * | 6/2010 | Suter | ................ | A61C 1/084 |
| | | | | 433/75 |
| 2010/0151412 A1 * | 6/2010 | Suter | ................ | A61C 8/0089 |
| | | | | 433/75 |
| 2012/0253353 A1 * | 10/2012 | McBride | ............ | A61B 17/1757 |
| | | | | 606/97 |
| 2017/0281320 A1 * | 10/2017 | Blackbeard | .......... | A61C 8/0025 |

FOREIGN PATENT DOCUMENTS

| | | | |
|---|---|---|---|
| KR | 2010001362 | * | 2/2010 |
| KR | 20130127319 A | * | 11/2013 |

* cited by examiner

SURGICAL GUIDING TOOL, METHOD AND KIT FOR PLACING DENTAL IMPLANTS

TECHNICAL FIELD

The invention pertains to the technical field of a surgical guiding tool for positioning dental implants, more particularly for placing pterygoid implants. Furthermore, the invention pertains to a method for placing dental implants, particularly pterygoid implants, using a surgical guiding tool. Lastly, the invention pertains to a kit for placing dental implants, particularly pterygoid implants.

BACKGROUND

Dental implants are an increasingly popular option for patients with missing teeth due to excessive decay, periodontitis, or accidents causing physical displacement and the like. Oral rehabilitations supported by dental implants provide an attractive alternative to mucosally supported dentures because they provide more stability and comfort during chewing, allowing patients to resume their normal diets. Furthermore they prevent bone loss due to disuse or incorrect loading of the bone by mucosally supported dentures.

In comparison to dentures and the like, however, dental implant procedures involve costly and complex surgical work. More accurately, dental implant procedures generally involve the placement of a dental implant in the underlying jawbone as a foundation, and the subsequent attachment of a prosthetic part to the implant above the gum line. Generally, an osteotomy must be performed to prepare the bone for placement of the implant. The implant is then inserted and fixed into the bone where it serves to hold the dental prosthetic part. The osteotomy and implant placement must be precise to avoid biological and prosthetic complications.

Inaccuracies in placing the osteotomy can damage nearby vital structures such as nerves, blood vessels, sinuses and neighboring teeth, or needlessly destroy bone. This is especially the case when dealing with pterygoid implants, as these implants are placed in the posterior part of the maxilla, an area with reduced visibility and accessibility, where the bone has very low density at the crestal level.

In fact, the steep learning curve and challenging technique is the only disadvantage of the pterygoid implant (Hernandez Alfaro F, 2013), making this therapeutic modality inaccessible for the average surgeon. Nevertheless, the advantages are numerous: bone grafts (sinus floor elevations) are avoided, maxillary sinus integrity is maintained, predictable results, can be executed under local anesthesia, prosthetic cantilevers are avoided, low morbidity, immediate loading of these implants is possible (drastically reducing treatment time from 6 or 9 months to less than 24 hours). Furthermore, while the morphology of the alveolar crest is highly variable due to atrophy and resorption, the anatomy of the buttress formed by the maxilla, the pyramidal process of the palatine bone and the pterygoid apophysis of the sphenoid bone is relatively constant and implant placement is therefore commonly performed under very specific angles.

Improper placement of the implant osteotomy may cause complications during the implant procedure. If the osteotomy is not placed in the proper position in the jawbone, further drilling may be necessary and primary implant stability may become problematic, endangering implant integration. Even more troublesome, if bone has been mistakenly removed, new bone may have to be grafted or added to the site and allowed to heal for 3-6 months before a new attempt can be made.

Positioning mistakes also require additional office visits by the patient, additional time before loading of the implants with the bridge or prosthesis, and unnecessary discomfort. For this reason, it is highly desirable to reduce the risk of drilling in an incorrect position.

Many tools and methods exist for increasing the accuracy, reliability, and ease with which a surgeon can perform the drilling operation. The most popular technique remains free-hand alignment. In the case of free-hand drilling, a surgeon draws upon his or her experience to determine the proper trajectory and final location of the implant. Because it is difficult to fully inspect the site, especially in the case of pterygoid implants, the surgeon typically has great difficulty in determining the proper position and angulation of the drill in this initial step, even after making a flap.

Model-based or lab-based methods allow improved positioning by allowing less invasive surveying of the implant site. This method also provides for transferring of the measurements from the cast to the actual site. An example of the prior art is U.S. Pat. No. 7,086,860 to Schuman et al. The Schuman method involves using tools to determine the size, angles, and positions for the dental implant on a model cast. The cast is cut to determine the bone position. A graphic is then drawn on the model and tools are used to transfer the placement information of the graphic to the implant site. In the laboratory, the buccal-lingual ("BL") volume of bone is derived from the subtraction of the tissue depth as measured in the mouth through bone sounding. If the anatomy is followed, an accurate reflection of the available bone volume for implant placement may be determined. The mesio-distal ("MD") positioning of the implant is derived from the transpositioning or translation of information from a radiograph onto the cast.

The above method has several limitations. The MD positioning in the lab is only an estimate and is not verifiable until transferred to a model and the mouth. Also, this method only allows the surgeon to practice drilling on a model and does not assist with transferring or accurately mapping the determined drilling position from the model back to the implant site. This technique is not possible for pterygoid implants as sound soft tissue references for bone sounding are not available in the soft palate. Furthermore, bone sounding in this area would be very painful and not complication-free.

U.S. Pat. No. 5,556,278 to Meitner is directed to a template to allow a surgeon to more accurately transfer the drilling location determined on the model to the implant site in the mouth. Meitner describes a tooth setup molded around the implant site and then placed on a cast model. The surgeon then drills through the setup. A guide post is inserted through the osteotomy, and a sleeve is inserted over the guide post. A resin is then placed over the entire site with a separating medium between the resin and model. Once the resin dries, the resin is removed and can be used as a template to transfer the exact location from the model to the implant site. Further, the guide sleeve may act as a radiographic marker so the surgeon can determine the location and trajectory of the osteotomy to be made in the bone by taking an X-ray with the template in place in the mouth.

Although the Meitner apparatus allows for relatively precise transfer of a drill location from a model to the implant site, errors still arise due to variations between the model and implant site. Whereas lateral errors might be acceptable for short and straight implants, they become problematic in the case of pterygoid (long and angulated) implants, more in particular at the implant apex due to angular deviations. Also, in the edentulous patient precise repositioning is troublesome. Further, the surgeon may decide on a position using the model and later reconsider when examining the X-ray with the template and sleeve positioned at the implant site. In this situation, the template must be formed again from the start and the patient will be required to make extra visits to the office, have further X-rays done and wait longer.

Another technique is based upon determining a trajectory for the drill using tools and aids and then translating the trajectory information to the implant site. An exemplar of such a technique is U.S. Pat. No. 5,015,183 to Fenick. Using X-rays, the surgeon determines where the implant should be positioned in the bone and then uses bushings to help guide the drill bit. Fenick also creates a radiology stent that includes an opaque grid. The stent, without any drill bushings, is X-rayed while in the patient's mouth. The stent is then placed over a model of the patient's jaw where the grid provides a frame of reference that helps in manually positioning a drill bit relative to the model jaw. A hole is drilled into the model, and the resulting hole helps align a drill bushing relative to the model. Next, a cast is created over the model to capture the drill bushing. The cast, with the drill bushing, is then placed in the patient's mouth to help guide the drill bit that drills a hole into the patient's jawbone. With the Fenick system, some positional accuracy may be sacrificed because the drill bushing is aligned to a model rather than being aligned directly to the patient's actual jaw.

In more recent years, computers and sophisticated peripheral imaging equipment have caused the positioning of implant systems to become far more sophisticated. Using Computed Tomography one can construct detailed computer models such as computer aided drafting (CAD) drawings. The computer allows technicians and surgeons to experiment with many different positions and trajectories in three-dimensional computer space. A computer also allows a user to calculate the exact trajectory for the drill. Moreover, once the model is constructed and trajectory calculated, the data can be used to prototype a surgical guide for the drill through computer aided manufacturing (CAM). A major drawback is that Computed Tomography Imaging is required, exposing the patient to a radiation dose much higher than with conventional dental radiology (e.g. panoramic X-ray).

Thus, computers in combination with many of the above procedures allow surgeons and technicians great flexibility in planning for the osteotomy and implant procedure. However, once the planning has been converted into the surgical guide, the surgeon is obliged to follow the planned trajectory rigidly or to continue free-handed if the surgical protocol needs adjustment. Translation of the data from the model to the implant site are not always error free, especially when long angulated (e.g.) pterygoid implants are considered. Further practical drawbacks for the use of CAD-CAM guides in the pterygoid area are: the need for longer drills with limited interarch space, bulky bushings and the need for posterior reinforcement of the guide. Besides, such equipment can be extremely costly. Also, sophisticated equipment requires sophisticated technical skills and may be beyond the reach of those with limited technology skills.

Another method for performing implant osteotomies provides a method for readjusting the drill trajectory directly in the mouth. U.S. Pat. No. 7,097,451 to Tang describes a thermoplastic surgical template that allows adjustment after initially setting a drill position. The Tang template includes a base and a drill guide. The alignment of the drill guide may be determined using conventional methods. Alternatively, the template may be fastened in the mouth without setting an initial drill position.

The Tang template is constructed of a thermoplastic chosen with thermo-properties such that it can be heated to a state whereupon it can be molded. The thermoplastic then hardens when it cools. Thus, the surgeon can place the template, heat the template, readjust the drill guide with a specified tool, and then allow it to harden at the determined position. This process minimizes the number of office visits and steps in the osteotomy procedure. Surgeons can easily adjust the template at will without going through lots of steps or fabricating procedures.

Although the Tang template allows a surgeon to combine modeling with relatively accurate translation of the data to the implant site, such templates and methods lack readjustment control. The surgeon can readjust the template at the mouth site, but readjustment amounts to free-hand alignment. Once the thermoplastic is heated to a moldable state, the template flows freely in all directions. Essentially, the surgeon must reposition the drill guide in free space, meaning, in three dimensions with 360° of rotation. Additionally, the abutment and temporary crown can only be made after the surgical guide has been approved clinically because of the liberal readjustment procedure. Similar to the other methods described, the Tang method does not provide a controllable and quantifiable method of positioning relative to a dental cast.

Some other documents have tried to provide a device for positioning dental implants but fail to do so however for the very unique situation for placing pterygoid dental implants. For instance, the Korean patent application KR 2013/0127319 A provides a type of drill guide which has two legs defining a direction for the drill to burrow into the jaw. However, as can be seen from the figures of the document, and especially in FIGS. 2 and 3 of the document, the device proposed in the application uses an abutment with two legs to embrace the drill (or part of a drill pathway) and to angle this pathway correctly. In said FIGS. 2 and 3 it is clear that the legs are intended to rest upon the gum tissue and underlying jawbone, and make no use of the unique bone structure in the pterygoid region. It is to be understood that, in the case of dental reconstruction such as placing and/or drilling for a pterygoid dental implant, this gum tissue is very likely to be deformed and thus would provide a variable base for the device for every patient. Even the slightest deformation of this base for the device would shift the drilling angulation which, as is known by one skilled in the art, could easily ruin the operation, causing an incorrect osteotomy and thereby requiring the grafting of new bone material and subsequent repeat of the original operation to create the osteotomy in the first place. Furthermore, as can be seen in said FIGS. 2 and 3, the device has no way of securing itself in any except for the steady hand of the user. Lastly, the application makes no mention of the use of this device for the placement of pterygoid dental implants (or the drilling therefor) and, from what can be seen from the angulation of the drill in FIG. 3, is not intended for such practices.

In a second document, US 2010/151411 A1, a similar device is provided as before, wherein the abutment and the two legs extend and form a lower region. Again, the abutment and the legs are meant to embrace a drill or shape a pathway for a drill, as can be seen in FIGS. 6 and 7 of the document for instance, by resting on the gum tissue and underlying jawbones. The lower region formed is configured to fit into a preformed drill hole, in order to steady the positioned device better and thereby provide a secure guide or pathway for the drill to perform further drilling (typically osteotomies are made by several subsequent drilling operations to either burrow deeper or to perform more delicate operations). The device therefore not only fails to be able to perform the initial action of functioning as a drill guide for a first drilling operation, as it needs a preformed osteotomy or a template (or drill jig) in order to secure the lower end of the abutment and the legs therein. These templates are often invasively secured (bone-supported CAD-CAM surgical guides). If they are mucosally supported, they often lack precision due to fixation errors and in case of pterygoid implants result in a magnification of angular deviations into extensive lateral apical errors. Lastly, and again, the proposed device would not be fit for the placement of pterygoid dental implants (or the drilling therefor) as from said FIG. 7, it is clear that the angulations of the pathway for the drill are incorrect, even more so as the application makes no mention of the use of the device for pterygoid dental implants. As known by one skilled in the art, the placement of pterygoid dental implants is much more delicate than other dental implants, as both the location is difficult to reach and the angulation needs to be exact.

In light of the forgoing, it would be beneficial to have a method and device for placing a pterygoid dental implant which overcomes the above and other disadvantages of known implant positioning systems and methods. What is needed is an improved method and apparatus for determining the ideal drilling trajectory that would allow accurately and repeatably performing a pterygoid dental implant procedure.

SUMMARY OF THE INVENTION

The devices and methods described in the background, excepting the free-hand techniques that have their obvious disadvantages of inaccuracy, danger of mistakes and/or accidents, all require extensive and/or expensive surgical guide systems to be modelled specifically for a patient, thereby often needing several scans, moldings or other time consuming preparatory procedures. Furthermore, said systems suffer from inaccuracy, due to the fact that the guide is positioned at the occlusal or mucosal level, thereby allowing large apical errors due to small angular deviations at the occlusal or mucosal level. The device as described in this document can be positioned via a minimally-invasive procedure that can be executed in a very short time. This goes for the removal of said device as well. The device described in this document can be constructed in a general model that will correctly enable positioning of a pterygoid implant for the majority of patients, or a few general models that will enable positioning for an even wider scope of patients, or lastly the device can be constructed via CAD/CAM techniques so as to fit exactly for a single patient. This last version will be specifically useful for beginning surgeons who wish to master the use of the device with maximal security.

In a first aspect, the present invention provides a device suitable for the subsequent positioning of a dental implant, comprising a handle extending along a longitudinal axis and having a proximal and a distal end, and a bifurcated abutment means at the distal end and at the proximal end of the handle. Each abutment means comprises two legs, whereby the configuration of the two legs on the proximal abutment means is mirrored with respect to the configuration of the legs on the distal end. Furthermore, a first of the bifurcated abutment means is adapted to embrace the buttress formed by the processus pyramidalis ossis palatini, the tuberosity of the maxilla and/or the processus pterygoideus ossis sphenoidalis on the left maxilla of a patient, a second of the bifurcated abutment means is adapted to embrace the buttress formed by the processus pyramidalis ossis palatini, the tuberosity of the maxilla and/or the processus pterygoideus ossis sphenoidalis on the right maxilla of a patient. By having an abutment means both on the proximal and on the distal end whereby the configuration of the legs is mirrored, the device can be used on both left and right side of the upper jaw. The term "mirrored" is intended to illustrate that the configuration of the legs and the abutment means is opposite on the proximal end in view of the legs and abutment means on the distal end so that the device can be used on both sides of the upper jaw (left and right maxilla). As the mentioned bone structures on the right and left maxilla (and the left and right maxilla themselves as well) are each other's mirror-symmetrical copies (or at least very substantially so), it is clear that mirroring the configurations on both ends in respect of each other, will allow (the abutment means of) one end to embrace the mentioned bone structure of the right maxilla and (the abutment means of) the other end to embrace the mentioned bone structure of the left maxilla. The meaning of the term "mirrored" is further made clear by the figures.

The handle and abutment means furthermore protect vulnerable soft tissues from harm. Also, should an incorrect drilling path be followed, the drill will encounter the handle and/or the abutment means, thus alerting the operator who is using the device by the vibrations caused by the operational drill touching the handle and/or the abutment means, whilst keeping the drill from going further and preventing unnecessary damage. The improvement of the proposed device firstly lies in the distinct shape of the abutment means, particularly the profile of the region of the abutment means between the legs, as this is configured specifically for embracing (along with the legs themselves) the buttress formed by the processus pyramidalis ossis palatini, the tuberosity of the maxilla and/or the processus pterygoideus ossis sphenoidalis. The bone structure here comprises the suture or fusion of the processus pterygoideus ossis sphenoidalis and the tuberosity of the maxilla, where the processus pyramidalis ossis palatini joins these structures. The very specific shape of this bone structure allows for a very accurate positioning of the device by embracing said bone structure with the abutment means and the legs, as the edge between the legs of the abutment means and the legs themselves are designed specifically for this purpose. This edge between the legs has a profile which is adapted to fit over the relief of the bone structure at the sutura pterygo-maxillaris, where the processus pterygoideus ossis sphenoidalis, the tuberosity of the maxilla and the processus pyramidalis ossis palatini join. As this suture of fusion is the narrowest point of the bone in the laterolateral cross section, and is located at an indent with respect to surrounding osseous structures, the device will necessarily be placed in the correct frontal plane. This will cause the position in which and the orientation under which the device is placed to be generally equal for most patients (notwithstanding severe anatomical aberrations). Thus it enables a generally applicable method of positioning the device according to a specific orientation and in a specific position. As the accuracy in positioning and in orientation of such an implant device are of the utmost importance, it is clear what advantages the proposed device provides. In a non-intrusive way, the device can be positioned to function as a guide for a drill or for a device for securing a dental implant in an osteotomy.

In contrast to any other device currently known in the state of the art, the proposed device of this invention guides the drilling and/or placement of an implant at the apical level of the implant instead of at the occlusal level. By guiding the implant and/or drilling at the apical level, angular deviations are greatly reduced since the implant/drill is guided at its most distal point (in view of the surgeon during implant procedure) in this technique instead of at the occlusal level and thereby at its most proximal point as is the case with the prior art devices. These deviations have been certified by several studies, for instance described in *"Image-based planning and clinical validation of zygoma and pterygoid implant placement in patients with severe bone atrophy using customized drill guides. Preliminary results from a prospective clinical follow-up study"* by Vrielinck et al (in the International Journal of Oral and Maxillofacial Surgery, February 2003; 32(1): 7-14) wherein unacceptable angular deviations were recorded for zygoma and pterygoid dental implants with devices that guide the implants on an occlusal level. The proposed device of the invention greatly reduces these deviations and thus allows a more accurate placement of the dental implant, and thereby enabling a more secure positioning of said implant.

Optionally, the device can be custom-made (for instance by CAD/CAM techniques, stereolithography, additive manufacturing, 3D printing) based on CT-imagery of the aforementioned bone structure of the patient in question, to allow the device to even better embrace the bone structure. This could allow the device to be function even more accurately and even for patients with deviating bone structures for whom the general version of the device would not function in a sufficient way.

Preferably, the bending angle of the longitudinal axis of the handle with respect to the plane wherein the two legs of one of the abutment means lie, is comprised between 10° and 90°, more preferably between 30° and 80°, most preferably either about 45° (or generally between 35° and 55°, or between 40° and 50°) or about 17.5° (or generally between 7.5° and 27.5°, or between 12.5° and 22.5°), whereby said bending angle is defined as the angle between the distal end of the longitudinal axis of the handle with respect to said plane. Said bending angle is the supplementary angle of the angle $\alpha_1$ in FIG. 1B and FIG. 2B or the angle $\alpha_2$ in FIGS. 1D and 2D. More preferably, the bending angle, $\beta_1$ or as can be seen in FIG. 1B and FIG. 2B or the angle $\beta_2$ in FIG. 1D or 2D, of the longitudinal axis of the handle with respect to the central axis of the footing of the abutment means, is smaller than the bending angle of the longitudinal axis of the handle with respect to respectively $\alpha_1$ or $\alpha_2$.

In a further embodiment, one of the legs, the first leg, of at least one abutment means, and preferably both abutment means, has a hook-shaped end adapted for embracing the posterior border of the lamina horizontalis ossis palatini. This will allow the device to be secured using the structure of the bones in the upper jaw of a patient. The lamina horizontalis ossis palatini has a thickened edge on its posterior border that reinforces said border and allows the device to exert some force on it. This hook-shaped end serves as an additional safety, ensuring the surgeon that the device is positioned correctly.

In a further embodiment, the second leg of at least one abutment means is generally straight or slightly bent. Said second leg is adapted to rest generally perpendicular with respect to the Frankfort plane against the lamina lateralis processus pterygoidei while the first leg is embracing the posterior border of the lamina horizontalis ossis palatini and the edge connecting the two legs is resting in the incisura pterygoidea against the part of the processus pyramidalis ossis palatini between the processus pterygoideus ossis sphenoidalis and the tuberosity of the processus alveolaris maxillae.

In a further embodiment, when an abutment means is embracing the buttress formed by the processus pyramidalis ossis palatini, the tuberosity of the maxilla and/or the processus pterygoideus ossis sphenoidalis as described in previous paragraph, the hook-shaped end of the first leg of said abutment means is adapted to allow rotation around the posterior border of the lamina horizontalis ossis palatini. This rotation can continue until a predetermined angulation of the longitudinal axis of the handle relative to the Frankfort plane is reached from a sagittal view. Said rotation is towards the lower jaw. Preferably the hook-shaped end is adapted to block further rotation and/or signify the operator when said predetermined angulation is reached.

In a further embodiment, said predetermined angulation is comprised between 30° and 60°, preferably comprised between 40° and 50°, and most preferably about 45°. This is a preferred angle for placing pterygoid dental implants as it allows the forces exerted during the operation to be mainly borne by stronger bone structures. By doing so, risk of complications is reduced, especially the risk for insufficient primary stability in order to load the pterygoid implant immediately. Moreover, this angulation allows the surgeon to place a longer implant, thus placing the neck of the implant more anteriorly, which might be more optimal from a prosthetic point of view.

In an alternative further embodiment, said predetermined angulation is comprised between 60° and 90°, more preferably between 65° and 80° and most preferably about 72.5°. This is a second preferred angle for placing pterygoid dental implants, as described above. The angle of 72.5° might be preferred if the surgeon wants to work without angulated abutment on the pterygoid implant and/or if the surgeon wants to diminish the divergence compared with other implants in the maxilla.

In a further preferred embodiment, the buccopalatal angulation of the longitudinal axis of the handle relative to the Frankfort plane is comprised between 65° and 110° from a frontal view when the device is embracing the buttress of the processus pyramidalis ossis palatini and the predetermined angulation is achieved. More preferably, said buccopalatal angulation is comprised between 70° and 100°, even more preferably between 75° and 90°. Most preferably, said buccopalatal angulation is about 81.3°.

In a further embodiment, at least one of the abutment means and its legs are made of an autoclavable material or a material that can be sterilized in any other way or disinfected. Preferably both abutment means and their legs are made of an autoclavable material or a material that can be sterilized or disinfected and most preferably, the entire device is made of such a material. If the device in such a material is cheap to manufacture, that is also fine.

In a further embodiment, the device comprises one or more mounting means for a drilling system, preferably adapted to allow said drilling system to move along the longitudinal axis of the handle. This will further guide the free-hand drilling, and will ensure a correct direction of drilling according to the preferred medical angulations as described above. Preferably a mounting means is provided for both abutment means, but alternatively a single mounting means can be shared. The mounting means can also allow a stationary drilling system to be mounted onto the device, whereby the drilling system is adapted to move the drill bit along the longitudinal axis of the handle. In a further preferred embodiment, the drilling system can be mounted on said mounting means at a variable position in the plane perpendicular to the longitudinal axis of the handle of the device. This allows an operator, when using the device, to choose the point of entry of a drill bit in the jawbone. The drilling system can be subsequently locked into said position, whereupon it can be moved parallel to the longitudinal axis of the handle, as mentioned above.

In a further preferred embodiment, at least one and preferably both of the abutment means has a bending angle of the central axis of said abutment means with respect to the longitudinal axis of the handle comprised between 10° to 90° (for instance between 20°, 30°, 40°, 50°, 60°, 70° and 80°) and is adapted to physically limit an optimal path for drilling and/or other procedures when in place on the processus pyramidalis ossis palatini.

In a further embodiment, the device comprises a mounting means for a suction and/or lighting means. Optionally, mounting means for other instruments that are used in the field of implantology can be included, or a single mounting means can be comprised in the device, suitable for mounting one or several of these instruments on.

In a further embodiment, the abutment means and legs are only present at the distal end of the handle, and said abutment means and legs are adapted to embrace the processus pyramidalis ossis palatini, the tuberosity of the maxilla and/or the processus pterygoideus ossis sphenoidalis. It may be easier or cheaper to manufacture a device with only one abutment means, thereby making it more interesting for practical use as some patients will only need implants on one side of the jaw.

The use of the device as described above for pterygoid dental implant procedures offers a much greater chance of success than free-hand procedures at a limited cost, as opposed to most known instruments that require higher dose irradiation of the patient, as well as expensive modelling and manufacturing with limited precision.

Note that in the description of the methods, it is implied that the device is introduced with the intended end first, depending on whether the left or right maxilla is operated on, as any person skilled in the art would readily understand.

In a second aspect, the invention provides a method for guiding a drilling system, using a device suitable for the subsequent positioning of a dental implant in a maxilla of a patient, comprising:
 a. a handle extending along a longitudinal axis and having a proximal and a distal end;
 b. and a bifurcated abutment means at the distal end of the handle, comprising two legs, whereby the bifurcated abutment means is adapted to embrace said maxilla at the processus pyramidalis ossis palatini and/or the processus pterygoideus ossis sphenoidalis and/or the tuberosity of said maxilla, said method comprising the following steps:
 a. administering an anesthetic to the patient;
 b. making an incision, preferably between 4 to 20 mm long in the mucosa, muscles and periosteum down to the bone;
 c. partially introducing the distal end of the device in the mouth of a patient, whereby the abutment means is introduced in the mouth of the patient;
 d. mounting the device onto the maxilla of the patient;
 e. positioning the device so that:
  a. an angulation of the longitudinal axis of the handle relative to the Frankfort plane of the patient from a sagittal view is reached either comprised between 30° and 90°, preferably either between 40° and 50° or 67.5° and 77.5°, most preferably either about 45° or 72.5°;
  b. and a buccopalatal angulation of the longitudinal axis of the handle relative to the Frankfort plane is reached comprised between 65° and 110° from a frontal view, preferably about 81.3°;
 f. drilling into the maxilla along the longitudinal axis of the handle; characterized in that mounting the device onto the maxilla of the patient is executed by embracing the processus pyramidalis ossis palatini and/or the tuberosity of the maxilla and/or the processus pterygoideus ossis sphenoidalis with the introduced abutment means.

In a third aspect, the invention provides a method for guiding a drilling system, using a device as described above, comprising the following steps:
 a. administering an anesthetic to a patient;
 b. accessing the jawbone of the patient by making an incision, preferably of about 4-20 mm in the mucosa, muscles and periosteum that outlines two separate mucoperiosteal flaps and reflecting said flaps, thereby exposing the bone underneath of the patient;
 c. partially introducing the device in the mouth of the patient, so that the appropriate abutment means is introduced in the mouth of the patient;
 d. embracing the buttress of the processus pyramidalis ossis palatini, the tuberosity of the maxilla and/or the processus pterygoideus ossis sphenoidalis with the introduced abutment means;
 e. positioning the device so that:
  a. an angulation of the longitudinal axis of the handle relative to the Frankfort plane of the patient from a sagittal view is reached comprised between 30° and 90°;
  b. and a buccopalatal angulation of the longitudinal axis of the handle relative to the Frankfort plane is reached comprised between 65° and 110° from a frontal view;
 f. drilling into the upper jaw along the longitudinal axis of the handle.

The advantages of this technique, and the device used for it, is that it allows for an easy, intuitive and non-intrusive positioning of the device in order to guide a drilling system so that the drilling system drills into the upper jaw under a correct angulation. As mentioned before, the bone structure for pterygoid dental implants is thinner than for other implants and therefore, it is of paramount importance that the osteotomy is created correctly and at the first try. Should the drill be angulated wrong, for instance by free-hand drilling techniques, either the implant will be positioned incorrectly and result in a prosthetically unfavorable outcome. Insufficient primary stability of the implant and/or non-integration could lead to the necessity to repeat the operation. This will in most events require new bone to be grafted onto the pterygoidal site as the remains after an incorrect osteotomy will not support a second drilling. Grafting new bone would be an expensive and painful consequence, and would create a further delay for the actual placement of the implant, which is very undesirable for most dental patients.

The same reasons as for the advantages of the device itself apply here, namely that, by using the distinct shape of the processus pyramidalis ossis palatini, the tuberosity of the maxilla and the processus pterygoideus ossis sphenoidalis, the device can embrace this unique bone structure configuration so that a placement in the correct frontal plane is ensured.

In a further embodiment, the invention provides a method for guiding a drilling system, using a device as described above, whereby said device comprises a first leg with a hook-shaped end as described above and a second leg as described above, whereby said method comprises following steps:
   a. administering an anesthetic to a patient;
   b. accessing the jawbone of the patient, preferably by making an incision of about 4-20 mm in the mucosa, muscles and periosteum that outlines two separate mucoperiosteal flaps and reflecting said flaps, thereby exposing the bone underneath of the patient;
   c. partially introducing the device in the mouth of a patient, so that the appropriate abutment means is introduced in the mouth of the patient;
   d. embracing the lamina horizontalis ossis palatini with the hook-shaped end of the first leg of the introduced abutment means;
   e. embracing the buttress of the processus pyramidalis ossis palatini, the tuberosity of the maxilla and/or the processus pterygoideus ossis sphenoidalis so that the edge of the introduced abutment means between the two legs rests against the part of the processus pyramidalis ossis palatini between the processus pterygoideus ossis sphenoidalis and the tuber of the processus alveolaris and the second leg rests against the lamina lateralis processus pterygoidei by rotating the device in the Frankfort plane of the patient;
   f. subsequently rotating the device in a parasagittal plane until:
      i. an angulation of the longitudinal axis of the handle relative to the Frankfort plane of the patient from a sagittal view is reached either comprised between 30° and 90°;
      ii. and a buccopalatal angulation of the longitudinal axis of the handle relative to the Frankfort plane is reached comprised between 65° and 110° from a frontal view;
   g. drilling into the upper jaw according to the direction of the handle of the device;
   h. optionally stopping the drilling when the drill reaches a drill stop.

Preferably, the device is adapted to only allow rotation until the angulations mentioned above are reached. This can be achieved by modeling the device so that further rotation will be physically blocked by the bone structure of the patient, for instance the lamina horizontalis ossis palatini stopping the further rotation by blocking the hook-shaped end or for instance the lamina lateralis of the pterygoid process blocking further rotation in the Frankfort plane.

In a fourth aspect, the invention provides a method for positioning a pterygoid dental implant, using a device as described above, according to one of the methods described above, subsequently comprising the following steps:
   a. securing the dental implant according to the direction of the handle of the device in the osteotomy created in previous steps;
   b. sealing off the dental implant with a cap or connecting it to either a healing abutment or an abutment and/or a prosthetic part ("immediate loading");
   c. closing the incision and the access to the jawbone;

Said methods, and particularly the device, are especially suitable for placing pterygoid dental implants. The methods described above are an improvement on known methods as the steps to position the device are minimally-invasive. Chiefly however, it is a vast improvement on the expensive common methods that require elaborate preparatory image taking, submitting patients to unnecessary irradiation and the manufacturing of an unnecessarily complex template designed specifically for each patient. These templates are often invasively secured (bone-supported CAD-CAM surgical guides). If they are mucosally supported, they often lack precision due to fixation errors and—in case of pterygoid implants—magnification of angular deviations into extensive lateral apical errors. The methods described in this document are of course more expensive than free-hand methods, but offer a much greater chance of success to the patient. As stated previously, said free-hand procedures are often less accurate and have a higher risk on mistakes and accidents.

In a fifth aspect, the invention provides a kit for placing dental implants, comprising one or more devices as described above, and one or more pterygoid dental implants. The kit can optionally also comprise a drilling system, a suction device, a lighting device and other instruments an implantologist would use during the placing of a dental implant, or a combination thereof.

DETAILED DESCRIPTION OF THE INVENTION

Figure 1A:
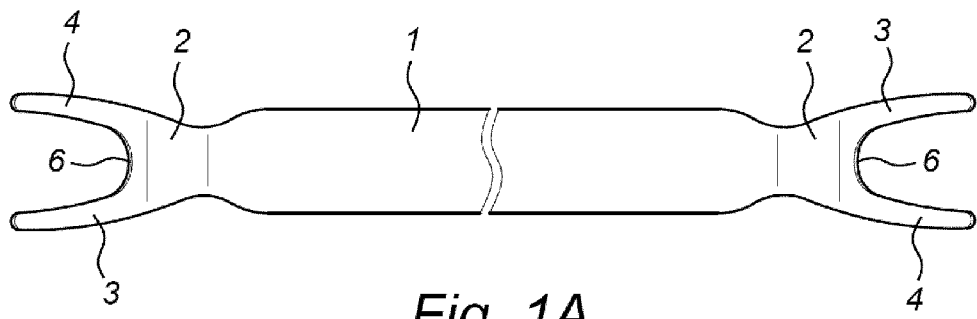
FIG. 1A shows an embodiment of the device from a top view.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The expression "about" as used herein referring to a measurable value such as a distance or angle, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

The expression "operatively coupled" or "operatively mounted" used describing an abutment means or the device, here and throughout the description unless otherwise defined, refers to a state wherein the abutment means is embracing the buttress of the processus pyramidalis ossis palatini, the tuberosity of the maxilla and/or the processus pterygoideus ossis sphenoidalis. The abutment means embracing the buttress of the processus pyramidalis ossis palatini, the tuberosity of the maxilla and/or the processus pterygoideus ossis sphenoidalis may include, in the case wherein the first leg of the abutment means comprises a hook-shaped end, said hook-shaped end embracing the posterior border of the lamina horizontalis ossis palatini. This may further include, in the case wherein the second leg of the abutment means is generally straight or slightly bent, said second leg resting against the lamina lateralis processus pterygoidei.

The expression "general" or "generally" or when referring to anatomical planes or axes of a person or structural planes or axes of the device used here and through the description unless otherwise defined, allows for deviations of about 15° as an anatomical structure can differ substantially from person to person. When referring to orientation with respect to anatomical structures, it is described for the case of an average person.

Furthermore, the device can be modified so as to differ from the described orientation without losing its functionality. The description should therefore be interpreted on basis of functionality, whereby given orientations can be considered as possible embodiments of the invention.

The term "mirrored" as used in the text to indicate the configuration of the abutment means (and the legs thereof) refers to the mirrored symmetry of the two abutment means (and the legs thereof) in order to be able to act on both sides of the maxilla of a patient. As the bone structures of the left and right maxilla are substantially equal, these can be seen as mirror symmetrical, and therefore the configuration of the two abutment means and the legs thereof should be mirror-symmetrical as in view of each other, since substantially the same shape and dimensions will need to be present in both, but only mirrored. This can be seen more clearly in the figures of this document.

The term "cap" herein refers to an element commonly placed on a dental implant after the dental implant has been placed. This may include but is not limited to, cover screws, healing abutments or healing caps, prosthetic abutments or prostheses.

The structure of the processus pyramidalis ossis palatini and its surrounding bony structures are well fitted for positioning and securing a device onto, to aid in placing dental implants under predetermined angles, due to the complex configuration of said bony structures. However, since this structure is often fragile, one has to be careful in choosing anchoring points. As mentioned before, the specific design of this bone structure allows the proposed device to be accurately positioned in an orientation and position that is very similar for most patients (notwithstanding extreme anatomical aberrations). The person skilled in the art will agree that, due to the presence of a fusion zone between the abovementioned bony elements, this region is singularly suited for accurately positioning and securing the proposed device in such a way that it can show an ideal path for the placement of a pterygoidal implant device, or an ideal path for a drill to create an osteotomy for a pterygoidal implant device (or for other tools in such a procedure).

The part of the processus pyramidalis ossis palatini between the processus alveolaris and the processus pterygoideus ossis sphenoidalis allows for an abutment means of the device to be placed that embraces said part of the processus pyramidalis ossis palatini. Again, the mentioned bone structure is ideally suited for being embraced by the abutment means of the device due to its specific build.

Particularly the reinforced posterior border of the thin lamina horizontalis ossis palatini is interesting for securing an abutment means of the device as it provides an additional anchoring point that can withstand a certain amount of force and pressure.

When using this reinforced posterior border as an anchoring point with the abutment means of the device embracing the previously described part of the processus pyramidalis ossis palatini, the design of the device allows for a stable positioning of the device onto the processus pyramidalis ossis palatini.

The present invention concerns a device for the subsequent positioning of a dental implant, more particularly a pterygoid dental implant, comprising a handle extending along a longitudinal axis, having a proximal and a distal end, and a bifurcated abutment means at the distal end and at the proximal end of said handle. Each bifurcated abutment means comprises two legs and the configuration of said two legs on the proximal abutment means is mirrored with respect to the configuration of the two legs on the distal end. Furthermore, a first of the bifurcated abutment means is adapted to embrace the left maxilla at the processus pyramidalis ossis palatini and/or the processus pterygoideus ossis sphenoidalis and/or the tuberosity of the left maxilla. The second of the bifurcated abutment means is adapted to embrace the right maxilla at the processus pyramidalis ossis palatini and/or the processus pterygoideus ossis sphenoidalis and/or the tuberosity of the right maxilla. By said embrace, the device can be steadied and enables a surgeon to drill and/or position the dental implant at the apical level instead of at the occlusal level, as is the case with the devices in the prior art. By guiding the drill and/or the dental implant at the apical level, angular deviations of the implant are greatly reduced, resulting in an increase in accuracy of the placement and thereby in a better implant position (both from an esthetical point of view as well as from a structural stability point of view considering that this region can be very brittle and allows very little room for deviation).

The handle, and more specific, the longitudinal axis of the handle, serves as a guide for the operator during the drilling and/or placement of the dental implant. As the positioning of the implant needs to be executed under very specific angles, as described previously in this document, the device greatly facilitates the procedure and will improve the accuracy as well as the safety of the procedure compared to a free-hand process. The use of two legs is ideal to embrace the processus pyramidalis ossis palatini, the tuberosity of the maxilla and/or the processus pterygoideus ossis sphenoidalis and protect the overlying soft tissue.

In a preferred embodiment, one of the legs of at least one, preferably of both, of the abutment means has a hook-shaped end adapted for embracing the posterior border of the lamina horizontalis ossis palatini. Even more preferably, said hook-shaped end has a small cross-section. Most preferably, the bend of said hook-shaped end generally lies in a plane parallel to the plane defined by the longitudinal axis of the handle and the central axis of the abutment means to which said first leg is attached.

In a preferred embodiment, the second leg of at least one, preferably both, of the abutment means is generally straight or slightly bent. Even more preferably, said second leg has a flattened side facing the first leg of the abutment means it is attached to. Most preferably, said second leg generally lies in a plane parallel to the plane defined by the longitudinal axis of the handle and the central axis of the abutment means to which said second leg is attached.

In a preferred embodiment, when the device is operatively coupled to the processus pyramidalis ossis palatini, the hook-shaped end is adapted to allow rotation of the device around the posterior border of the lamina horizontalis ossis palatini until a predetermined angulation of the longitudinal axis of the handle relative to the Frankfort plane from a sagittal view is reached. Preferably, said rotation is in a plane generally parallel to the sagittal plane and directed towards the lower jaw. The buccopalatal angulation of the longitudinal axis of the handle relative to the Frankfort plane is comprised between 65° and 110° from a frontal view. Most preferably, said buccopalatal angulation is about 81.3°.

In preferred embodiments, said predetermined angulation is comprised either between 30° and 90°. Preferably, they are comprised either between 40° and 50° or between 67.5° and 77.5°. Most preferably, said predetermined angulation is either about 45° or about 72.5°. This is the current accepted standard in the field for pterygoid implants. Should other angulations be included or replace said standard, it is obvious that the device can easily be adapted to allow other angulations.

In a preferred embodiment, at least one, preferably both, of the abutment means and its legs are made of an autoclavable material or a material that can be sterilized in another way or disinfected. Preferably the entire device is made of such a material. This allows sterilization of the device, thereby allowing repeated use of the device without danger of contaminants remaining.

In a preferred embodiment, the device comprises a mounting means for a drilling system, preferably adapted to allow said drilling system to move along the longitudinal axis of the handle. This will enable an operator to follow the desired orientation of drilling more efficiently and easier. Preferably, the device has two such mounting means for both the distal end and for the proximal end. Alternatively preferably, the device has a single mounting means that can be used for the distal end as well as for the proximal end, for instance by making the device mirror-symmetrical with respect to a plane perpendicular to the longitudinal axis of the handle.

In a further embodiment, the device is adapted to physically limit a maximal drilling depth. This can be achieved for instance by including a solid plane in the abutment means adapted to block the path of a drill moving along the longitudinal axis of the handle at a predetermined point. Said predetermined point is at a drilling depth suitable for receiving an implant with a length of comprised between 10 mm and 35 mm, and preferably about 15 to 25 mm. An alternative embodiment includes a mounting means that allows distal movement of a drilling system along the longitudinal axis of the handle up to a certain point. This way, the drilling depth can be perfectly controlled by a surgeon operating the drilling system.

In a further embodiment, the device comprises mounting means for any instrument a practitioner in the field of implantology would need for drilling for and/or subsequent placing of a dental implant. These instruments may include a suction system, an illumination system but are not limited to these.

In a further embodiment, the device only comprises an abutment means and legs at the distal end of the handle, whereby said abutment means is adapted to embrace the processus pyramidalis ossis palatini, the tuberosity of the maxilla and/or the processus pterygoideus ossis sphenoidalis. As said, this may be more economic and easier to use for an operator.

In a further embodiment, the device is constructed based on images of the skull from a patient, more particular of the area around the upper jaw and specifically the posterior part of the maxilla and/or processus pyramidalis ossis palatini and/or processus pterygoideus ossis sphenoidalis. The images used can be X-ray images and/or other. The device can be constructed using CAD/CAM techniques, whereby both subtractive processes such as CNC milling, and additive processes such as 3D printing, can be used for the construction.

In a second aspect, the invention concerns a method for guiding a drilling system as described in the Summary, using a device as described above.

In a third aspect, the invention concerns a method for positioning a dental implant as described in the Summary, using a device as described above.

In a fourth aspect, the invention concerns a kit for placing implants, comprising one or more device as described above, and one or more dental implants. Preferably, said dental implants are pterygoid dental implants. As said, the kit can optionally also comprise other instruments an implantologist would use during the drilling for and placing of a dental implant, or a combination thereof.

The invention is further described by the following non-limiting examples which further illustrate the invention, and are not intended to, nor should they be interpreted to, limit the scope of the invention.

EXAMPLES

Preface

Figure 3A:
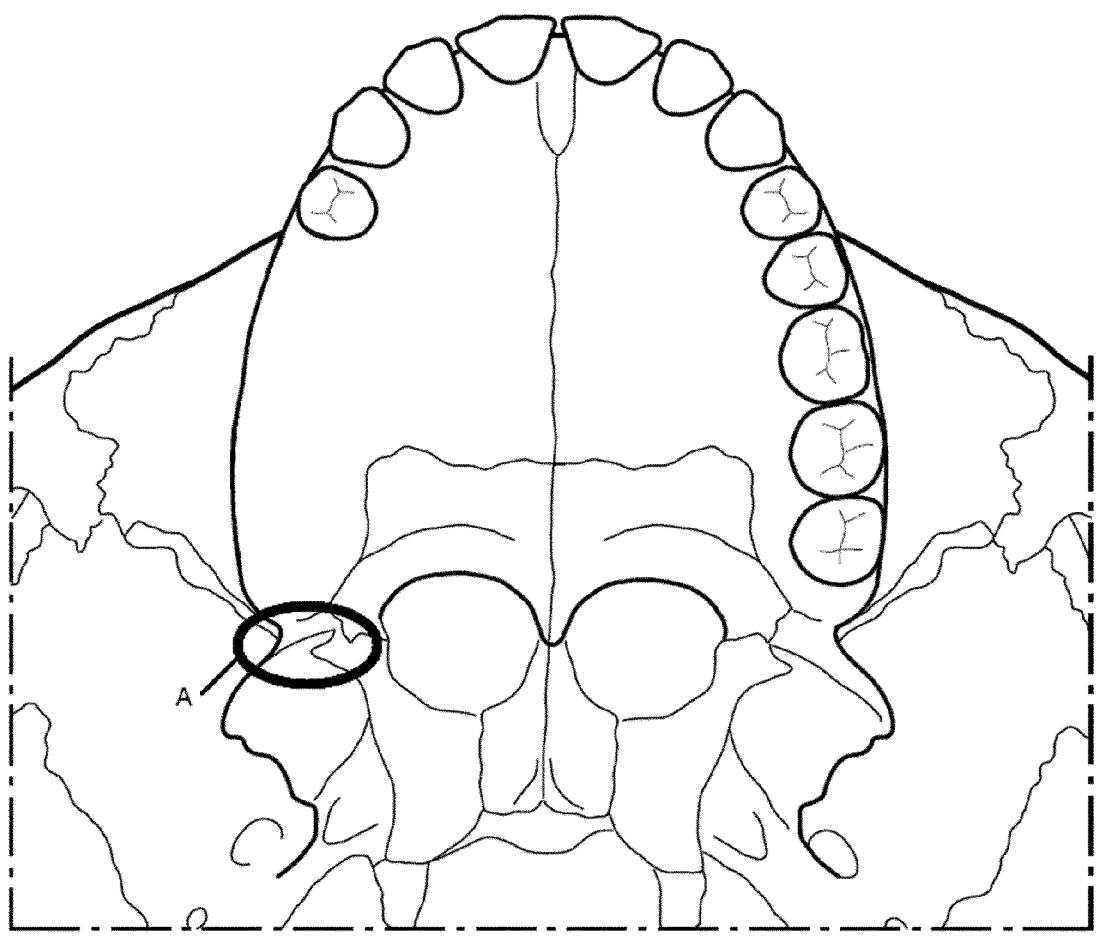
FIG. 3A shows an inferior view of a patient's skull.
Figure 3B:
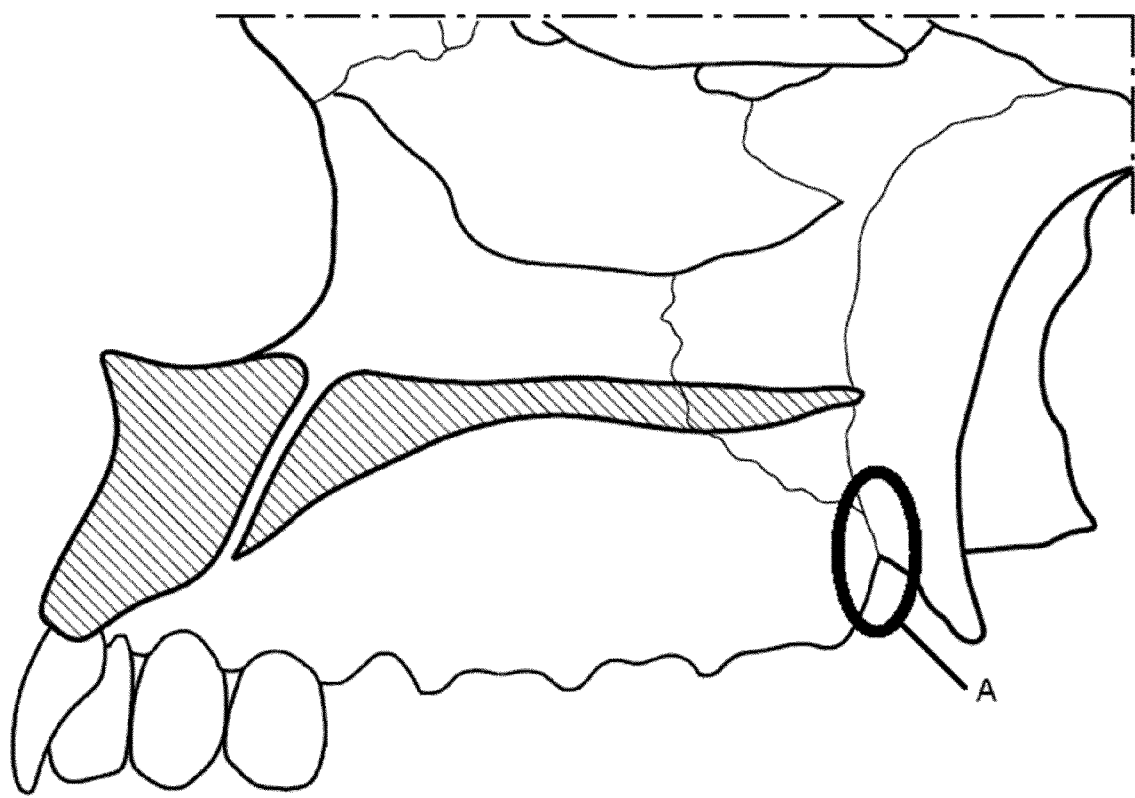
FIG. 3B shows a cross-sectional sagittal view of a patient's skull from an internal standpoint.
Figure 3C:
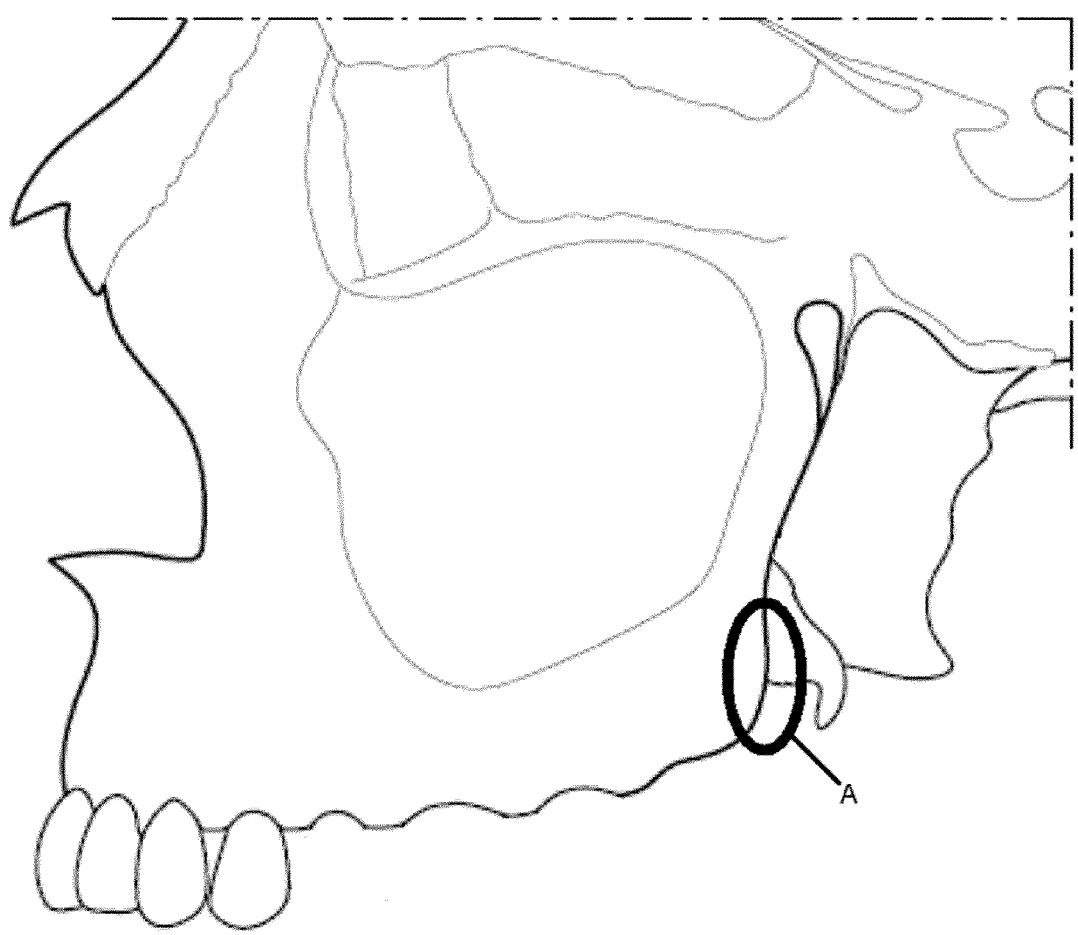
FIG. 3C shows a lateral view of a patient's skull from an external standpoint.

In FIGS. 3A, 3B and 3C, several views of a human skull are shown, whereby the human skull is lacking several teeth on the right maxilla. The conclusions of the examples hold for both maxillae or for the edentulous maxilla, as can be readily understood by the person skilled in the art. The mentioned drilling systems or implants or other tools, though not explicitly depicted in the figures, can be readily visualized by the person skilled in the art, with the longitudinal axis of such a dental tool parallel to the longitudinal axis of the handle of the device and moving generally parallel to said longitudinal axis of the handle of the device during part of the procedure (for instance during the actual drilling).

In the aforementioned FIGS. 3A, 3B and 3C, a zone (A) is indicated with an ellipse where the abutment means and/or the legs of the abutment means are designed to embrace the right maxilla. This is the bony structure of the processus pyramidalis ossis palatini and/or the processus pterygoideus ossis sphenoidalis and/or the tuberosity of the right maxilla. Said fusion of the aforementioned osseous structures, as can be seen from the different viewpoints, provides a very advantageous location for securing the proposed device in a manner that allows very little variation in angulation with respect to the jawbone. While the examples are generally described with a device that is configured to place dental implants at about 45° from the longitudinal axis of the implant with respect to the Frankfort plane (7) of the patient from a sagittal view, it is expected that any person skilled in the art could easily use the proposed technique for other preferred angulations (such as the commonly accepted alternative of about 72.5°).

Example 1

Figure 1B:
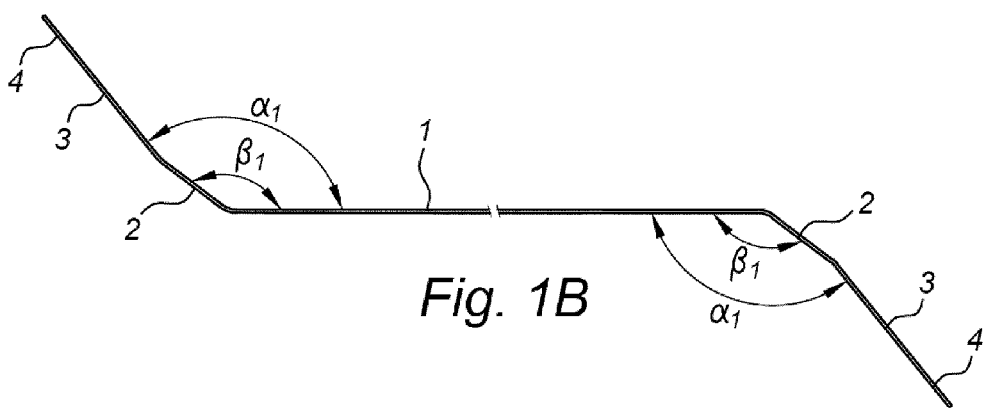
FIG. 1B shows the device of FIG. 1A from a side view along the short axis.
Figure 1C:
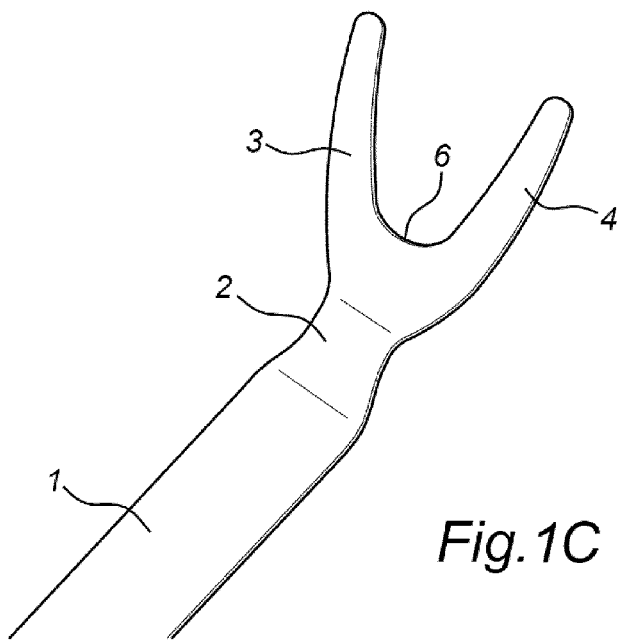
FIG. 1C shows a sectional view of the abutment means and legs on the abutment means of an embodiment of the device of FIGS. 1A and 1B.

The device described herein is shown in FIGS. 1A, 1B and 1C. It is suitable for the subsequent positioning of a dental implant, more specifically pterygoid dental implants and comprises a handle (1) extending along a longitudinal axis with a proximal and a distal end, whereby said handle (1) is about 150 mm long, about 20 mm wide and has a thickness of about 1.5 mm. The long handle (1) allows for easy manipulation by the operator, while the restricted width and thickness enable introducing the device in the mouth easily. The handle (1) is made this wide as this will show a clear guiding trajectory for a drilling system or other instruments to follow but will not inconvenience its use or the patient when positioned in the mouth. Different dimensions are however possible, for instance a length comprised between 80 mm up to 250 mm (or even beyond this range), a width comprised between 5 mm and 35 mm, or between 10 mm and 30 mm (or beyond these ranges) and/or a thickness comprised between 0.5 and 10 mm (or beyond this range). The long handle (1) allows for easy manipulation by the operator, while the restricted width and thickness enable introducing the device in the mouth easily. The handle (1) is made this wide as this will show a clear guiding trajectory for a drilling system or other instruments to follow but will not inconvenience its use or the patient when positioned in the mouth. Also, a mounting means for a drilling system or other instruments can be included onto said handle (1). The device further comprises a bifurcated abutment means (2) at the distal and at the proximal end of the handle, each comprising two legs, whereby the bifurcated abutment means (2) are adapted to embrace the processus pyramidalis ossis palatini, the tuberosity of the maxilla and/or the processus pterygoideus ossis sphenoidalis of a patient. Specifically, it is the interdigital edge (6) that is designed to optimally fit on the aforementioned bone structure, while the legs (3, 4) complete the embrace of the bone structure. The device is constructed generally symmetric with respect to a plane perpendicular to the longitudinal axis of the handle. This will enable the device to be used on both sides of the jaw of the patient. However, it is perfectly imaginable to provide the device with only a bifurcated abutment means on the one (distal) end of the handle, which might allow for an easier handling of the device and could reduce costs for patients who need a custom-made device for only either their left jaw or their right jaw. The device is rigid as it is crucial for the device to provide a stable trajectory for the placement of dental implants and not bend when pressure is applied onto the device.

Figure 1D:
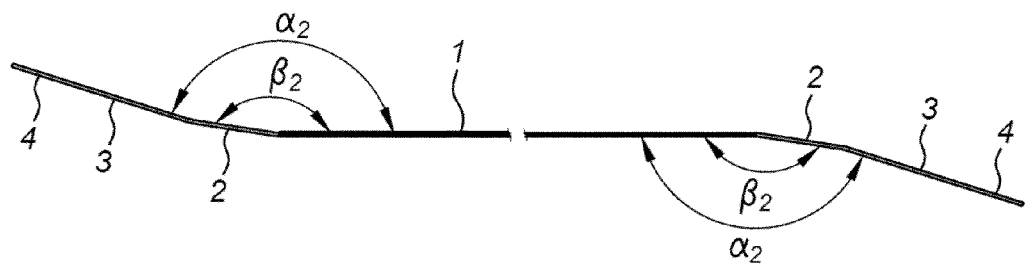
FIG. 1D shows an alternative embodiment of the device from a side view along the short axis for a different implant angulation.

In the following description, only one abutment means (2), the one on the distal end, and its legs will be discussed as the device is constructed symmetrically as stated above. This is shown in FIG. 1C. It will be referred to herein as the abutment means. Furthermore, the device will be described for an implant angle of 45°, as can be seen in FIG. 1A-1B-1C. The angles for the second implant angle of 72.5° will be displayed between parentheses, and the device can be seen in FIG. 1D.

The abutment means (2) is attached to the distal end of the handle (1), and the central axis of the abutment means has a bending angle of about 45° (17.5°) with respect to the longitudinal axis of the handle.

The following description is of the device when mounted onto a patient's processus pyramidalis ossis palatini, as this may require slightly different dimensions and angulations per patient.

The interdigital edge (6) between the two legs is adapted to rest against the part of the processus pyramidalis ossis palatini between the processus pterygoideus ossis sphenoidalis and the processus alveolaris. The first leg (3) is adapted to rest against the processus pyramidalis ossis palatini. The second leg (4) is adapted to rest against the lamina lateralis processus pterygoidei, while the interdigital edge (6) and the first leg (3) are positioned as stated above. This will be referred to as the secured position. Note that due to the shape of this bone structure, the combination of the interdigital edge (6), which is shaped to fit optimally against the bone structure, with the two legs (3, 4), which are designed in order to optimally embrace the bone structure, allows for a steady and secured positioning of the device whereby the drilling region, more specifically the apical drilling region for the implant, is as desired for further procedures.

The abutment means is adapted specifically to have an interdigital edge and legs which correspond with the profile of the incisura of the fusion of the tuberosity of the maxilla and the lamina lateralis and the lamina medialis of the processus pterygoideus so that the device is positioned correctly and allows for a correct angulation of a drill or implant device along the axis of the handle (depending on which of exact angulation is preferred or chosen in the operation, the handle is angled differently with respect to the abutment means, as mentioned before).

This position is achieved when an angulation of about 45° (72.5°) is achieved of the longitudinal axis of the handle with respect to the Frankfort plane (7) of the patient from a sagittal view. This is the desired position. The buccopalatal angulation of the longitudinal axis of the handle relative to the Frankfort plane (7) from a frontal view should be about 81.3° when the device is in the desired position. The device can be shaped to comply with these requirements, either based on the general anatomy of the human skull, or can be manufactured specifically for a patient on the basis of medical imaging of the skull of the patient.

Example 2

Figure 2A:
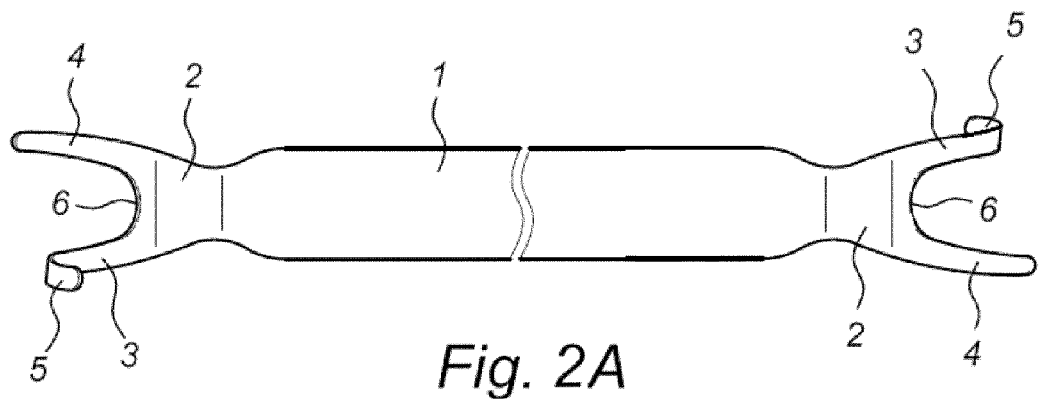
FIG. 2A shows an embodiment of the device with a leg with a hook-shaped end from a top view.
Figure 2B:
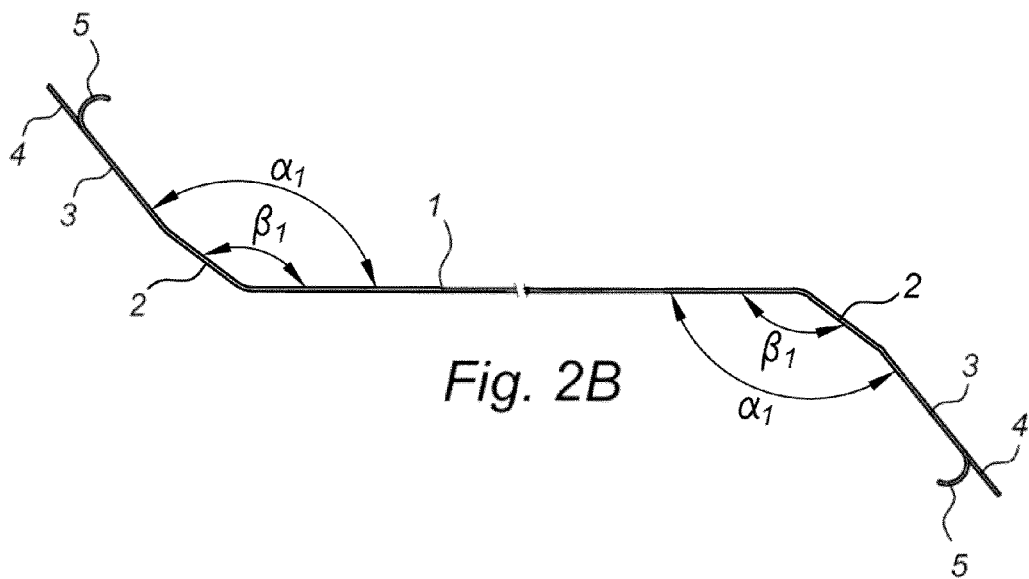
FIG. 2B shows the device of FIG. 2A from a side view along the short axis.

The device described herein is shown in FIG. 2A, FIG. 2B. It is suitable for the subsequent positioning of a dental implant, more specifically pterygoid dental implants and comprises a handle (1) extending along a longitudinal axis with a proximal and a distal end, whereby said handle (1) is about 150 mm long, about 20 mm wide and has a thickness of about 1.5 mm. As in the previous example, the long handle (1) allows for easy manipulation by the operator, while the restricted width and thickness enable introducing the device in the mouth easily. The handle (1) is made this wide as this will show a clear guiding trajectory for a drilling system or other instruments to follow but will not inconvenience its use or the patient when positioned in the mouth. Also, a mounting means for a drilling system or other instruments can be included onto said handle (1). The device further comprises a bifurcated abutment means (2) at the distal and at the proximal end of the handle, each comprising two legs, whereby the bifurcated abutment means (2) are adapted to embrace the processus pyramidalis ossis palatini, the tuberosity of the maxilla and/or the processus pterygoideus ossis sphenoidalis of a patient. The device is constructed generally symmetric with respect to a plane perpendicular to the longitudinal axis of the handle. This will enable the device to be used on both sides of the jaw of the patient. The device is rigid as it is crucial for the device to provide a stable trajectory for the placement of dental implants and not bend when pressure is applied onto the device.

Figure 2C:
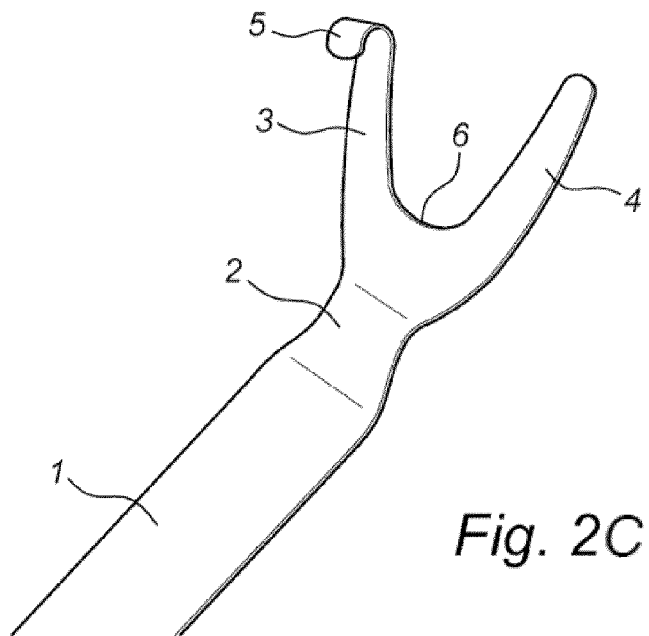
FIG. 2C shows a sectional view of the abutment and legs on the abutment means of an embodiment of the device of FIGS. 2A and 2B.
Figure 2D:
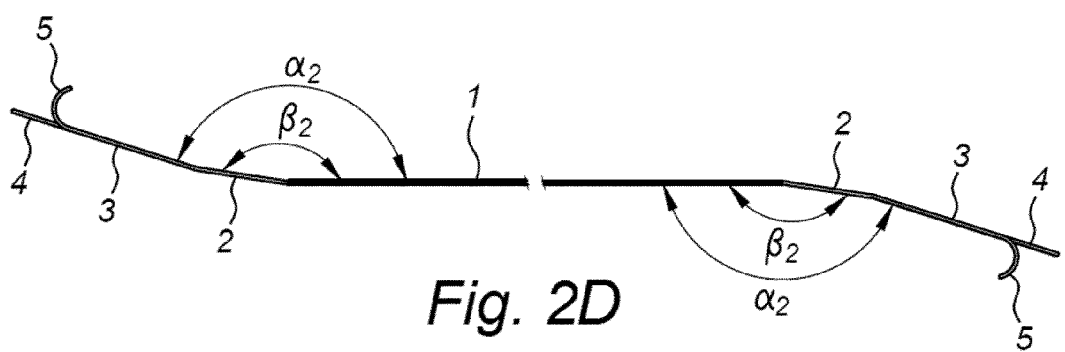
FIG. 2D shows an alternative embodiment of the device from a side view along the short axis for a different implant angulation.

In the following description, only one abutment means (2), the one on the distal end, and its legs will be discussed as the device is constructed symmetrically as stated above. This is shown in FIG. 2C. It will be referred to herein as the abutment means. Furthermore, the device will be described for an implant angle of 45°. The angles for the second implant angle of 72.5° will be displayed between parentheses, and the device can be seen in FIG. 2D.

The abutment means (2) is attached to the distal end of the handle (1), and the central axis of the abutment means has a bending angle of about 45° (17.5°) with respect to the longitudinal axis of the handle.

The first leg (3) of the abutment means has a hook-shaped end (5), adapted for embracing the posterior border of the lamina horizontalis ossis palatini. The hook-shaped end (5) has a bending angle of about 180° (152.5°) with respect to the longitudinal axis of the handle, as can be seen in FIG. 2B. Here, the bending angle is the angle between the distal end of the longitudinal axis of the handle and (the continuation of) the hook-shaped end (5). The second leg (4) of the abutment means is generally straight or slightly bent. The edge between the first and the second leg will be referred to as the interdigital edge (6). Other shapes may also be suitable for the second leg (4) as will become clear from the functional description that follows.

The following description is of the device when mounted onto a patient's processus pyramidalis ossis palatini, as this may require slightly different dimensions and angulations per patient.

The hook-shaped end (5) of the first leg is adapted to rest against and embrace the posterior border of the lamina horizontalis ossis palatini while the interdigital edge (6) between the two legs rests against the part of the processus pyramidalis ossis palatini between the processus pterygoideus ossis sphenoidalis and the processus alveolaris. The second leg (4) is adapted to rest against the lamina lateralis processus pterygoidei, while the interdigital edge (6) and the first leg (3) are positioned as stated above. This will be referred to as the secured position.

Figure 5A:
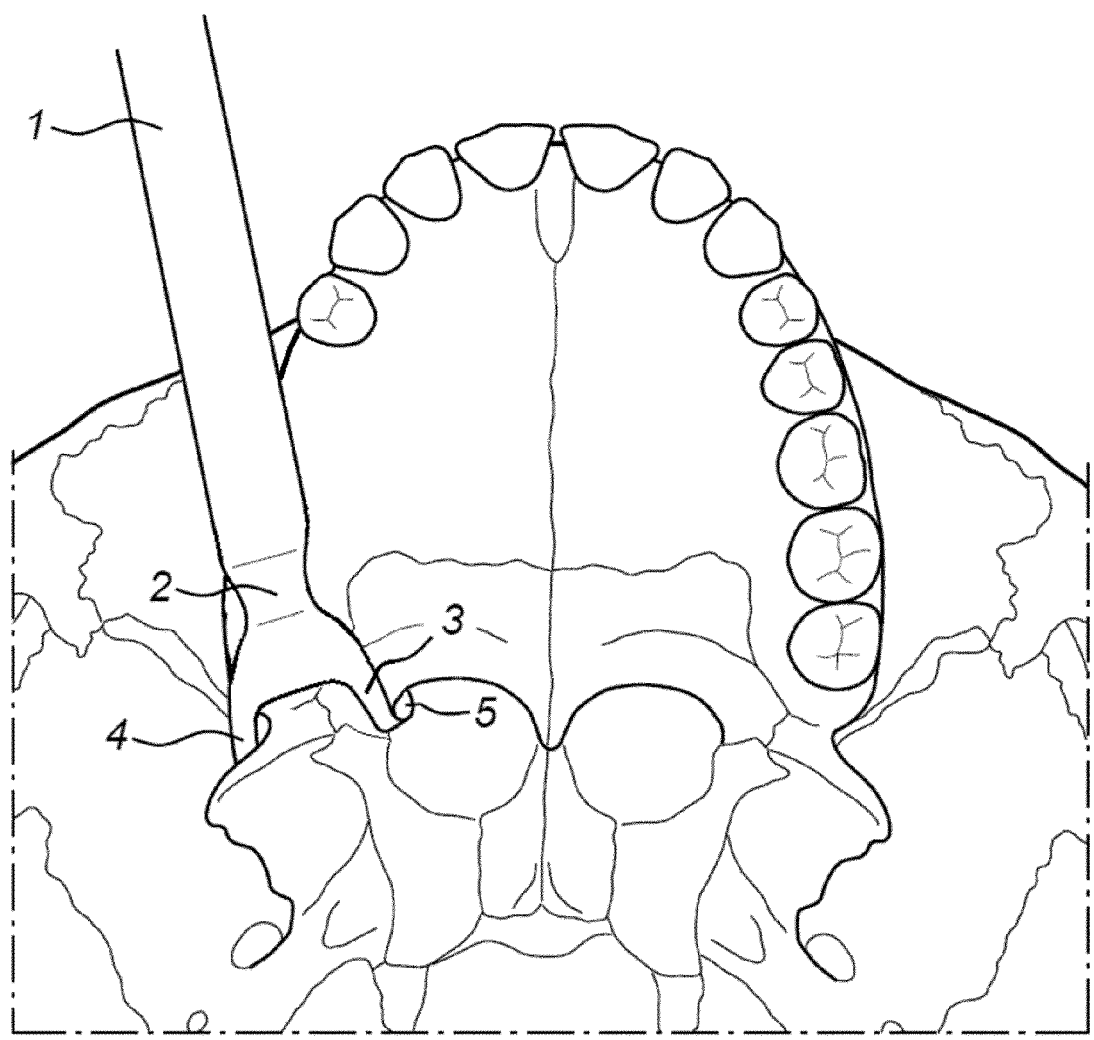
FIG. 5A shows an inferior view of a patient's skull with an alternative embodiment of the device (with a leg with a hook-shaped end) when mounted on the right side of a patient's upper jaw.
Figure 5B:
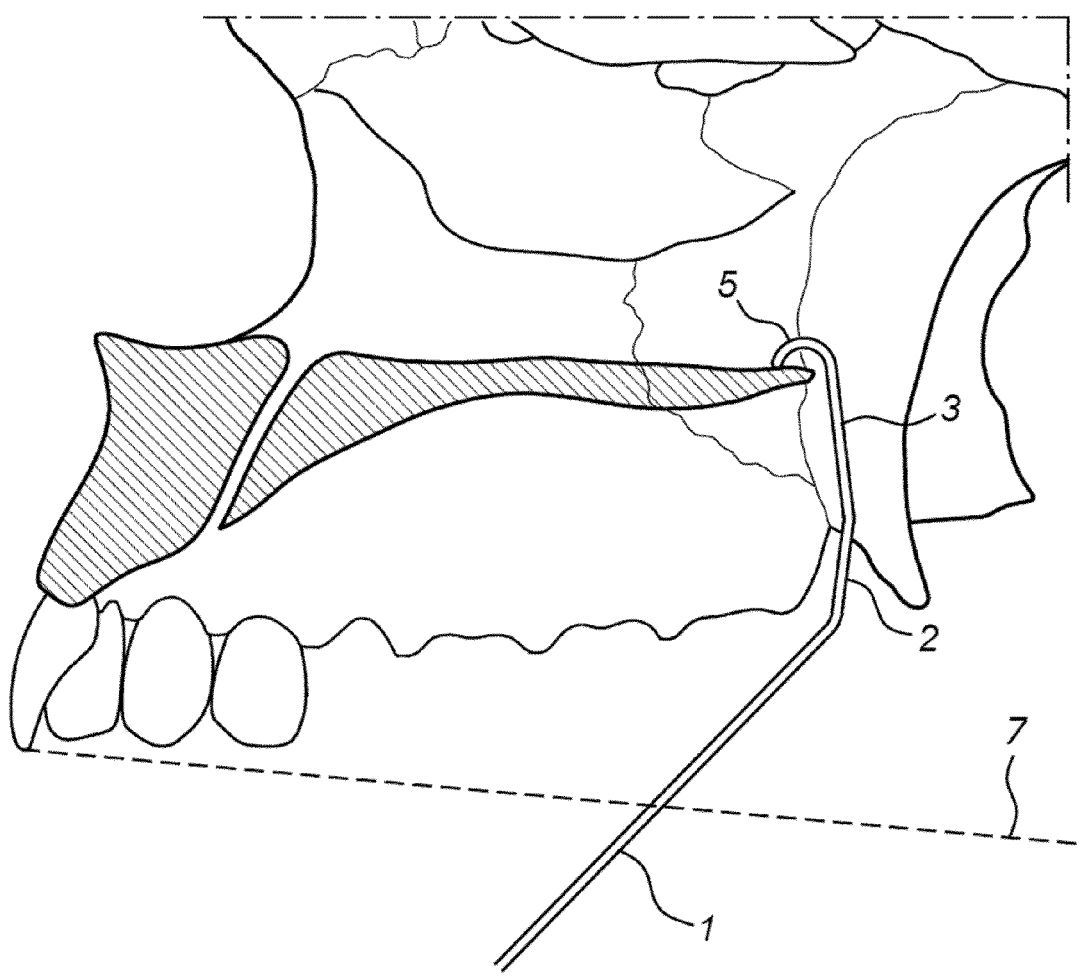
FIG. 5B shows a cross-sectional sagittal view from an internal standpoint, with the alternative embodiment of the device of FIG. 5A when mounted on the right side of a patient's upper jaw.

Furthermore, the hook-shaped end (5) is adapted to allow rotation of the device, when in secured position, around an axis defined by the point where the interdigital edge (6) rests against the part of the processus pyramidalis ossis palatini as stated above, and the point where the hook-shaped end (5) rests against the posterior border of the lamina horizontalis ossis palatini, as is visible in FIG. 5A and FIG. 5B. This rotation is only allowed until a maximal angulation of about 45° (or 72.5° depending on the desired implant angulation) is achieved of the longitudinal axis of the handle with respect to the Frankfort plane (7) of the patient from a sagittal view. This is the desired position. The buccopalatal angulation of the longitudinal axis of the handle relative to the Frankfort plane (7) from a frontal view should be about 81.3° when the device is in the desired position. The device can be shaped to comply with these requirements, either based on the general anatomy of the human skull, or can be manufactured specifically for a patient on the basis of medical imaging of the skull of the patient.

Example 3

What follows is a method for guiding a drilling system for drilling an osteotomy for receiving an implant, using the device described in Example 2.

No specifics will be gone into concerning anesthetics as this allows for much variation in the exact substance, the amount used and its application mode.

In an initial step after the administration of an anesthetic, a surgeon or dentist will access the bone in the region where the implant will be placed, making one or more incisions that allow two or more separate flaps to be reflected, thereby exposing the jaw bone underneath. Alternatively a second technique can be used to expose the bone by making a circular incision and removing the circular section of the mucosa. This second option is less invasive, but requires more certainty on the conditions of the bone underneath and will make the positioning of the device more difficult. Other options exist, however, these two are predominant in use.

The device is introduced into the mouth of the patient with the distal abutment means (2) and its legs first. Next the device is to be retracted slightly so the hook-shaped end (5) of the first leg embraces the posterior border of the lamina horizontalis ossis palatini. This is the first anchoring point for the device. Next, the abutment means (2) is rotated in the Frankfort plane (7) of the patient so that the second leg (4) rests against the lamina lateralis processus pterygoidei. In the following step, the abutment means (2) is rotated in the parasagittal plane so that the interdigital edge between the two legs (6) of said abutment means (2) rests against the part of the processus pyramidalis ossis palatini between the processus pterygoideus ossis sphenoidalis and the processus alveolaris, thereby reaching the secured position as mentioned earlier. The device cannot be pulled towards the operator any further as the hook-shaped end (5) is embracing the posterior border of the lamina horizontalis ossis palatini. Now the device is rotated further in the parasagittal plane of the patient until the desired position is reached. As said before, this position requires a buccopalatal angulation of the longitudinal axis of the handle relative to the Frankfort plane (7) of the patient from a frontal view comprised between 65° and 110°. Said buccopalatal angulation preferably is about 81.3° but can vary slightly from patient to patient. The desired position further requires an angulation of the longitudinal axis of the handle relative to the Frankfort plane (7) of the patient from a sagittal view either comprised between 30° and 60° or between 60° and 90°. Preferably said angulation is either 45° or 72.5°, but can again vary from patient to patient.

Figure 5C:
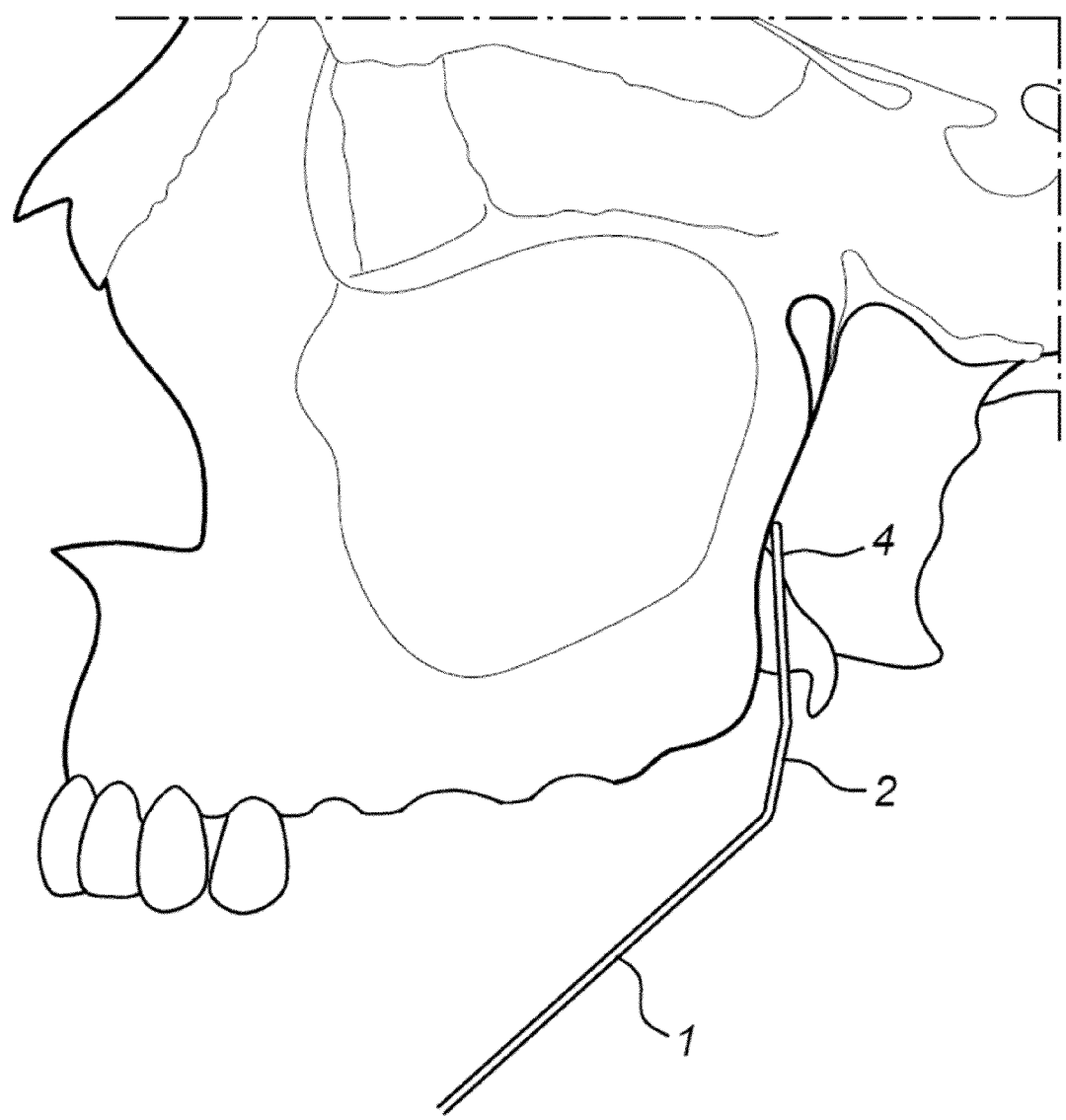
FIG. 5C shows a lateral view from an external standpoint, with an alternative embodiment of the device of FIGS. 5A and 5B when mounted on the left side of a patient's upper jaw.

Once the device reaches this desired position, as shown in FIGS. 5A, 5B and 5C, the handle (1) now defines a preferential drilling axis, which allows an operator to follow the handle (1) with the drill, thereby ensuring a stable and correct angulation. As stated several times before, for pterygoid implants this angulation is crucial as the jawbone is very thin in this region and therefore very fragile and weak.

Generally a small round bur or pointed drill will make a divot in the bone, by penetrating the bone's outermost layer. This will allow the following drills to be positioned easily. In a next step a pilot drill makes a pilot osteotomy to serve as a guide for other drills used later on. Alternatively a hand driven osteotome (either with or without the use of a hammer) or a piezo-electric device can be used instead of drills. Optionally the alignment of the pilot osteotomy can be evaluated by inserting an alignment pin into the pilot osteotomy to check the orientation of the osteotomy being created. After this, the pilot osteotomy is completed to full length needed for the dental implant. This drilling depth can be checked by markings on the operator's drill or a depth gauge, or by being stopped when the drill reaches a drill stop. The alignment pin can be used again to confirm the orientation and can also be used to ensure a correct drilling depth by markings on the pin. The drilling is usually performed in several steps with drills of incremental diameter to prevent overheating of the bone. The drilling can be concluded by threading the osteotomy created in the jawbone. This is done by using a thread-forming tool, or so-called screw tap to create threads on the walls of the osteotomy matching those on the implant. Some implants are self-tapping and create these threads as they are screwed into place, therefore, this last step is not necessary should such an implant be used. If the implant is self-drilling, there might not even be a need to drill and the implant might be installed by hand pressure alone under guidance of the proposed tool. Usually, the tooth implant site is flushed during the drilling with a sterile saline solution to absorb of heat being generated by the drilling. Alternatively mallets or piezo-electric tools can be used to prepare the osteotomy, as mentioned before.

Example 4

What follows is a method for guiding a drilling system for drilling an osteotomy for receiving an implant, using the device described in Example 1 or other parts of the application, where no hook-shaped end of a leg is present. Again, no specifics concerning the anesthetics used are discussed.

Figure 4A:
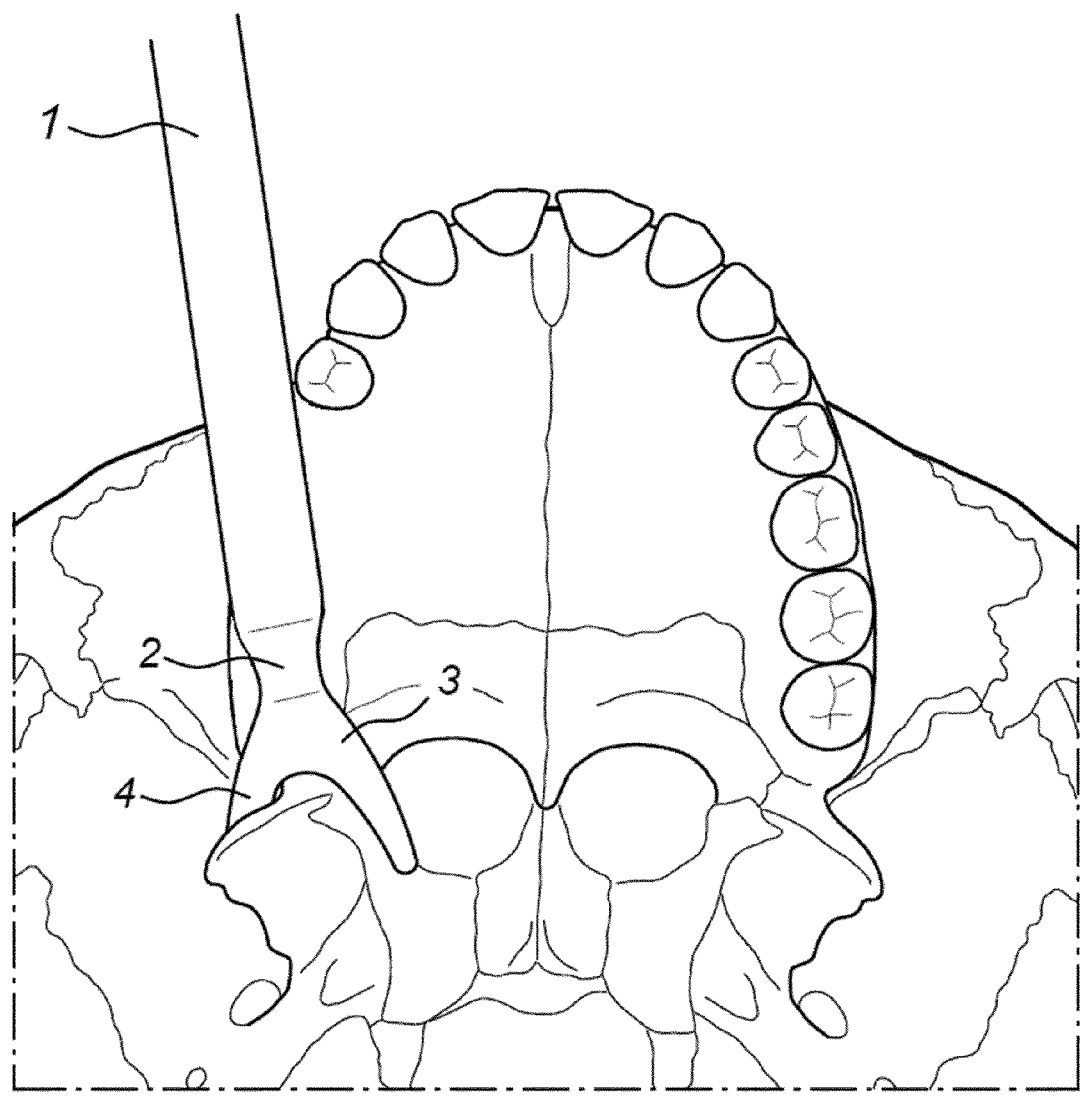
FIG. 4A shows an inferior view of a patient's skull, with an embodiment of the device when mounted on the right side of a patient's upper jaw.
Figure 4B:
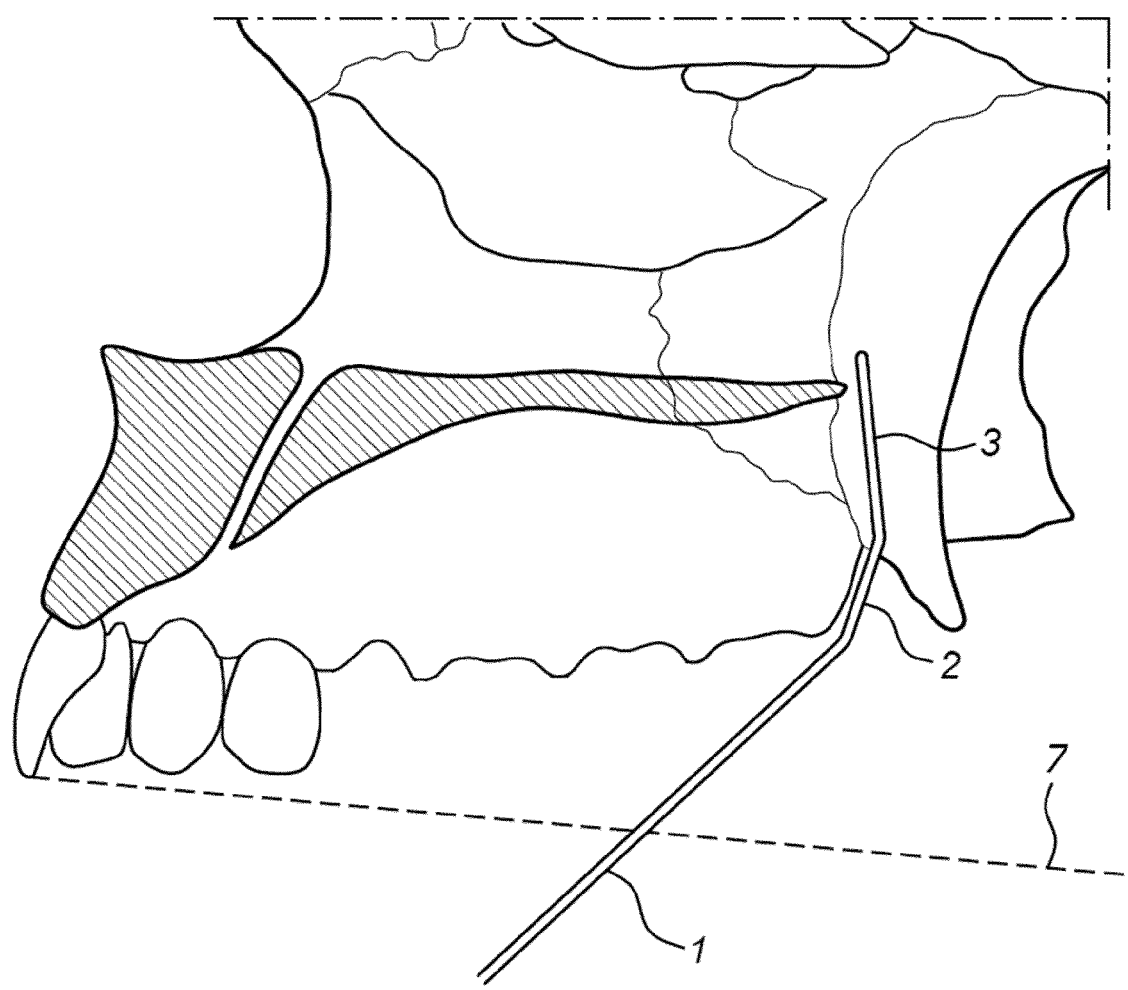
FIG. 4B shows a cross-sectional sagittal view from an internal standpoint, with an embodiment of the device when mounted on the right side of a patient's upper jaw.
Figure 4C:
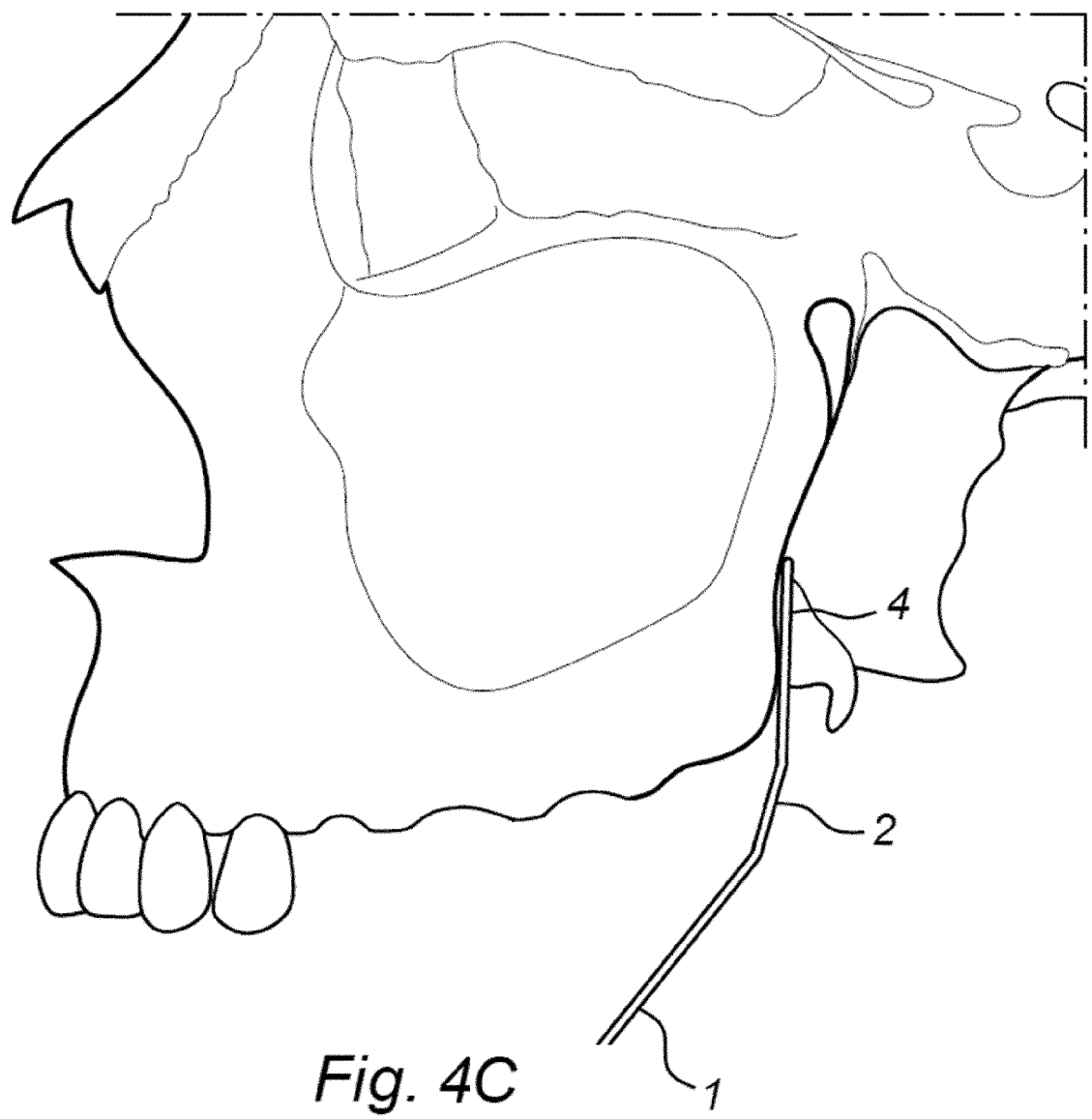
FIG. 4C shows a lateral view from an external standpoint, with an embodiment of the device when mounted on the left side of a patient's upper jaw.

The device is introduced into the mouth of the patient through the incision with the distal abutment means (2) and its legs first. It is positioned so that the distal abutment means and its legs embrace the fusion of the processus pterygoideus ossis sphenoidalis, the tuberosity of the maxilla and/or the processus pyramidalis ossis palatini. The shape or profile of the interdigital edge (6) is specifically adapted in order to optimally embrace this bone structure. Most optimally, the device, and said edge (6) is custom-made based on medical images of the patient, which guarantees a perfect fit and therefore, a perfect placement of the device. Through the shape of the distal abutment means and its legs, and the specific bone structure where it is placed, an accurate placement in the correct frontal plane is ensured. The handle (1) is configured with respect to the abutment means so that it allows for an optimal drilling path for a drill once the device is in place. This means that an angulation of the longitudinal axis of the handle relative to the Frankfort plane (7) of the patient from a sagittal view is reached either comprised between 30° and 90°, preferably either between 40° and 50° or 67.5° and 77.5°, most preferably either about 45° or 72.5°. Furthermore, this means that a buccopalatal angulation of the longitudinal axis of the handle relative to the Frankfort plane (7) is reached comprised between 65° and 110° from a frontal view, preferably about 81.3°. A possible secure position of the device according to the method of this Example 3 can be seen in FIG. 4A, 4B or 4C. Note that the person skilled in the art would readily implement the proposed method for a different angulation of the pterygoid dental implant, as it is known that there are a few options for the placement thereof.

The procedures following the positioning of the device can be similar to the ones proposed in Example 3 and will not be expanded upon therefore.

Example 5

What follows is a method for positioning a dental implant, in particular a pterygoid implant, using the device described in Example 1 or 2. The procedure described herein is in general identical to the one described in Example 3, but includes a step wherein the operator places a dental implant in the osteotomy created in previous steps. This is usually done using a surgical drilling unit via a special adapter on the hand piece of the surgical drilling unit for holding the dental implant, or can be done manually using a hand wrench. The implant is threaded matching the threads on the walls of the osteotomy, or can be a self-tapping implant which creates its own threads while being screwed into place. When the dental implant has been secured in the osteotomy, the operator will screw a so-called cover screw or healing abutment or prosthetic abutment or prosthesis onto the exposed portion of the dental implant to seal its internal aspects off from the oral environment. Subsequently, the mucoperiosteal flaps can be trimmed and/or shaped and repositioned back over the patient's jawbone and over or around the dental implant. Sutures can be placed to hold the soft tissue in place.

It is supposed that the present invention is not restricted to any form of realization described previously and that some modifications can be added to the presented example of fabrication without reappraisal of the appended claims. For example, if an extra leg is added to the abutment means for securing the position of the instrument in the mouth of a patient further, this addition holds no novelty or inventiveness over the instrument as proposed in this document.

The invention claimed is:
1. A device suitable for the subsequent positioning of a pterygoid dental implant, comprising:
 a. a handle extending along a longitudinal axis and having a proximal and a distal end; and
 b. a bifurcated abutment at the distal end and at the proximal end of the handle also extending along the same longitudinal axis of the handle, each of the bifurcated abutment comprising two legs; wherein
  a first of the bifurcated abutment is adapted to encircle left maxilla at the processus pyramidalis ossis palatini and/or the processus pterygoideus ossis sphenoidalis and/or the tuberosity of the left maxilla, and is adapted to fit over a relief in bone structure at sutura pterygomaxillaris of the left maxilla, and
  a second of the bifurcated abutment is adapted to encircle right maxilla at the processus pyramidalis ossis palatini and/or the processus pterygoideus ossis sphenoidalis and/or the tuberosity of the right max- illa, and is adapted to fit over a relief in the bone structure at the sutura pterygomaxillaris of the right maxilla; and whereby the second leg of at least one abutment is generally straight or slightly bent.

2. A device according to claim 1, whereby one of the legs, the first leg, of at least one abutment has a hook-shaped end adapted for encircling a posterior border of the lamina horizontalis ossis palatini.

3. A device according to claim 2, whereby, when an abutment is encircling the processus pyramidalis ossis palatini and/or the processus pterygoideus ossis sphenoidalis and/or the tuberosity of the maxilla, the hook-shaped end of the first leg of said abutment is adapted to allow rotation of the device around the posterior border of the lamina horizontalis ossis palatini until a predetermined angulation of the longitudinal axis of the handle relative to the Frankfort plane is reached from a sagittal view, whereby said rotation is towards lower jaw, and whereby the buccopalatal angulation of the longitudinal axis of the handle relative to the Frankfort plane is comprised between 65° and 110° from a frontal view.

4. A device according to claim 3, wherein said predetermined angulation is comprised between 30° and 60°.

5. A device according to claim 3, wherein said predetermined angulation is comprised between 60° and 90°.

6. A device according to claim 1, whereby at least one of the abutment and the legs are made of an autoclavable material or a material that can be sterilized in any other way or disinfected.

7. A device according to claim 1, whereby the device is capable of being mounted by a drilling system, piezo-electric device and/or mallets, and allow said drilling system, piezo-electric device and/or mallets to move along the longitudinal axis of the handle.

8. A device according to claim 1, whereby the relative angulations of the abutment, the first legs, the second legs and the handle with respect to each other, are based on measurements provided by medical imaging of a patient.

9. A device according to claim 1, whereby the device is capable of being mounted by a lighting and/or a suction and/or instruments used in the field of implantology.

10. A device according to claim 1, wherein the abutment is only present at the distal end of the handle and said abutment is adapted to encircle the processus pyramidalis ossis palatini and/or the processus pterygoideus ossis sphenoidalis and/or the tuberosity of the maxilla for either the left maxilla or the right maxilla.

11. A method for guiding a drilling system, using a device suitable for the subsequent positioning of a pterygoid dental implant in a maxilla of a patient, comprising:
  a. a handle extending along a longitudinal axis and having a proximal and a distal end;
  b. and a bifurcated abutment at the distal end of the handle also extending along the same longitudinal axis of the handle, comprising two legs, whereby the bifurcated abutment is adapted to encircle said maxilla at the processus pyramidalis ossis palatini and/or the processus pterygoideus ossis sphenoidalis and/or the tuberosity of said maxilla, and is adapted to fit over a relief in the bone structure at the sutura pterygomaxillaris of the right maxilla; and
  whereby the second leg of at least one abutment is generally straight or slightly bent;
  said method comprising the following steps:
    a. administering an anesthetic to the patient;
    b. making an incision, between 4 to 20 mm long in the mucosa, muscles and periosteum down to the bone;
    c. partially introducing the distal end of the device in the mouth of a patient, whereby the abutment is introduced in the mouth of the patient;
    d. mounting the device onto the maxilla of the patient;
    e. positioning the device so that:
      a. an angulation of the longitudinal axis of the handle relative to the Frankfort plane of the patient from a sagittal view is reached either comprised between 30° and 90°, either between 40° and 50° or 67.5° and 77.5°, or either about 45° or 72.5°;
      b. and a buccopalatal angulation of the longitudinal axis of the handle relative to the Frankfort plane is reached comprised between 65° and 110° from a frontal view, or about 81.3°;
    f. drilling into the maxilla along the longitudinal axis of the handle;
  wherein mounting the device onto the maxilla of the patient is executed by encircling the processus pyramidalis ossis palatini and/or the tuberosity of the maxilla and/or the processus pterygoideus ossis sphenoidalis with the introduced abutment.

12. A method for guiding a drilling system, using a device suitable for the subsequent positioning of a pterygoid dental implant, comprising:
  a. a handle extending along a longitudinal axis and having a proximal and a distal end;
  b. and a bifurcated abutment at the distal end and at the proximal end of the handle, each comprising two legs, whereby a first of the bifurcated abutment is adapted to encircle the left maxilla at the processus pyramidalis ossis palatini and/or the processus pterygoideus ossis sphenoidalis and/or the tuberosity of the left maxilla, and is adapted to fit over a relief in the bone structure at the sutura pterygomaxillaris of the left maxilla; and whereby a second of the bifurcated abutment is adapted to encircle the right maxilla at the processus pyramidalis ossis palatini and/or the processus pterygoideus ossis sphenoidalis and/or the tuberosity of the right maxilla, and is adapted to fit over a relief in the bone structure at the sutura pterygomaxillaris of the right maxilla; and
  whereby the second leg of at least one abutment is generally straight or slightly bent;
  said method comprising the following steps:
    a. administering an anesthetic to a patient;
    b. making an incision, between 4 to 20 mm long in the mucosa, muscles and periosteum down to the bone;
    c. partially introducing the device in the mouth of a patient, so that the appropriate abutment is introduced in the mouth of the patient;
    d. mounting the device onto the upper jaw of the patient;
    e. positioning the device so that:
      a. an angulation of the longitudinal axis of the handle relative to the Frankfort plane of the patient from a sagittal view is reached either comprised between 30° and 90°, either between 40° and 50° or 67.5° and 77.5°, or either about 45° or 72.5°;
      b. and a buccopalatal angulation of the longitudinal axis of the handle relative to the Frankfort plane is reached comprised between 65° and 110° from a frontal view, or about 81.3°;
    f. drilling into the upper jaw along the longitudinal axis of the handle;

wherein mounting the device onto the upper jaw of the patient is executed by encircling the processus pyramidalis ossis palatini and/or the tuberosity of the maxilla and/or the processus pterygoideus ossis sphenoidalis with the introduced abutment.

13. A method for guiding a drilling system, using a device according to claim 3, comprising the following steps:
   a. administering an anesthetic to the patient;
   b. making an incision, between 4 to 20 mm long in the mucosa, muscles and periosteum down to the bone;
   c. partially introducing the device in the mouth of a patient, so that the appropriate abutment k introduced in the mouth of the patient;
   d. encircling the lamina horizontalis ossis palatini with the hook-shaped end of the first leg of introduced abutment;
   e. encircling the processus pyramidalis ossis palatini so that an edge of the introduced abutment between the two legs rests against the part of the processus ossis palatini between the processus pterygoideus and the processus alveolaris and the second leg rests against the lamina lateralis processus pterygoidei;
   f. rotating the device in the Frankfort plane of the patient;
   g. rotating the device in the sagittal plane of the patient until:
   a. an angulation of the longitudinal axis of the handle relative to the Frankfort plane of the patient from a sagittal view is reached either comprised between 30° and 90°;
   b. and a buccopalatal angulation of the longitudinal axis of the handle relative to the Frankfort plane is reached comprised between 65" and 110° from a frontal view;
   h. drilling into the upper jaw according to the direction of the handle of the device;
   i. optionally stopping the drilling when the drill reaches a drill stop.

14. A method for positioning a pterygoid dental implant, according to claim 13, subsequently comprising the following steps:
   a. securing the pterygoid dental implant according to the direction of the handle of the device in the osteotomy created in previous steps;
   b. sealing off the pterygoid dental implant with a cap or connecting it to either a healing abutment or an abutment and/or a prosthetic part;
   c. closing the incision and the access to the jawbone.

15. A kit for placing pterygoid dental implants, comprising one or more devices according to claim 1, and one or more pterygoid dental implants.

* * * * *